United States Patent
Nilsson et al.

(10) Patent No.: US 6,781,029 B2
(45) Date of Patent: Aug. 24, 2004

(54) TRANSGENIC ANIMAL AND METHODS

(75) Inventors: Lars Nilsson, Uppsala (SE); Huntington Potter, Tampa, FL (US); Gary W. Arendash, Lutz, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/903,993

(22) Filed: Jul. 13, 2001

(65) Prior Publication Data

US 2002/0066117 A1 May 30, 2002

Related U.S. Application Data

(60) Provisional application No. 60/218,054, filed on Jul. 13, 2000.

(51) Int. Cl.[7] .................. A01K 67/027; G01N 33/15; C12Q 1/02
(52) U.S. Cl. .................. 800/14; 800/8; 800/12; 800/3; 435/4
(58) Field of Search .................. 800/14, 8, 12, 800/3; 435/4

(56) References Cited

U.S. PATENT DOCUMENTS

| | | | |
|---|---|---|---|
| 5,276,059 A | 1/1994 | Caughney et al. | 514/647 |
| 5,297,562 A | 3/1994 | Potter | 128/898 |
| 5,429,947 A | 7/1995 | Merril et al. | 436/518 |
| 5,434,170 A | 7/1995 | Andrulis, Jr. | 514/323 |
| 5,449,604 A | 9/1995 | Schellenberg et al. | 435/6 |
| 5,506,097 A | 4/1996 | Potter et al. | 435/4 |
| 5,535,760 A | 7/1996 | Potter | 128/898 |
| 5,571,671 A | 11/1996 | Potter | 435/6 |
| 5,705,401 A | 1/1998 | Masters et al. | 436/518 |
| 5,731,284 A | 3/1998 | Williams | 514/8 |
| 5,753,624 A | 5/1998 | McMichael et al. | 514/12 |
| 5,773,220 A | 6/1998 | DeKosky et al. | 435/6 |
| 5,817,626 A | 10/1998 | Findeis et al. | 514/12 |
| 5,830,670 A | 11/1998 | De la Monte et al. | 435/712 |
| 5,849,560 A | 12/1998 | Abraham | 435/219 |
| 5,854,215 A | 12/1998 | Findeis et al. | 514/12 |
| 5,958,883 A | 9/1999 | Snow | 514/16 |
| 5,981,208 A | 11/1999 | Tamburini et al. | 435/23 |
| 5,986,054 A | 11/1999 | St. George-Hyslop et al. | 530/350 |
| 6,043,283 A | 3/2000 | Giulian | 514/617 |

FOREIGN PATENT DOCUMENTS

| | | |
|---|---|---|
| WO | WO 94/24266 | 10/1994 |
| WO | WO 97/46664 | * 12/1997 |

OTHER PUBLICATIONS

Kuljis et al. Alzheimer–like diffuse amyloid plaques can be induced in transgenic mice expressing human alpha–1–antichymotrypsin. Society for Neuroscience Abstracts, (1993) vol. 19, 1–3, pp. 1035.*

Mucke et al. Potential roles of alpha1–antichymotrupsin and alpha–synuclein in Alzheimer's pathogenesis assessed in bigenic mice expressing human amyloid precursor proteins.Soc. Neurosci. Abstr., (1999) vol. 25, No. 1–2, pp. 302.*

Yeung et al. Alzheimer–like diffuse amyloid placues can be induced in transgenic mice expressing human alpha–1–antichymotrypsin. Society for Neuroscience Abstracts, (1993) vol. 19, No. 1–3, pp. 1035.*

Nilsson et al. Alpha–1–antichymotrypsin promotes beta–sheet amyloid plaque deposition in a transgenic mouse model of Alzheimer's disease. J Neurosci. Mar. 1, 2001;21(5):1444–51.*

Doetschman T. Interpretation of phenotype in genetically engineered mice. Lab Anim Sci. Apr. 1999;49(2):37–43.*

Kobayashi et al. Effect of alpha 1–antichymotrypsin on the toxicity of beta–amyloid fragment 25–40 in rat primary cultured neurons. Neurosci Lett. May 19, 1994;172(1–2):147–50.*

Anger W.K. Animal test systems to study behavioral dysfunctions of neurodegenerative disorders. Neurotoxicology. 1991 Fall;12(3):403–13.*

Abrham, $\alpha_1$–Antichymotrypsin is associated solely with amyloid deposits containing the $\beta$–protein. Amyloid and Cell Localization of $\alpha_1$–Antichymotrypsin, Neurobiology of Aging, Jun. 13, 1989, vol. 11, 123–129.

Abraham, Immunochemical identification of the serine protease inhibitor $\alpha_1$–Antichymotrypsin in the brain amyloid deposits of Alzheimer's disease, Cell, Feb. 26, 1988 vol. 52, 487–501.

Akiyama, Inflammation and Alzheimer's disease, Neurobiology of Aging 21, Jan. 17, 2000, 383–421.

Bales, Apolipoprotein E is essential for amyloid deposition in the $APP^{V717F}$ transgenic mouse model of Alzheimer's disease, PNAS, Dec. 21, 1999, vol. 96 (26) 15233–15238.

Bales, Neuroinflammation and Alzheimer's disease: critical roles for cytokine/A$\beta$–induced glial activation, NF-$\kappa$B, and apolipoprotein E, Neurobiology of Aging 21, Mar. 20, 2000, 427–432.

Bales, Lack of apolipoprotein E dramatically reduces amyloid $\beta$–peptide deposition, Nature Genetics, Nov. 1997, vol. 17 263–264.

(List continued on next page.)

Primary Examiner—Anne-Marie Falk
Assistant Examiner—Daniel M. Sullivan
(74) Attorney, Agent, or Firm—Saliwanchik, Lloyd & Saliwanchik

(57) ABSTRACT

A transgenic animal, preferably a mouse, that expresses human antichymotrypsin (ACT) in brain tissues is provided, together with animal tissue-derived cell lines and progeny animals of said transgenic animal. Progeny are obtained by mating the transgeny animal with select animal strains used as models of Alzheimer's disease, related neurological disorders, or amyloidogenic diseases. Methods utilizing the parent and progeny animals and cells derived therefrom are disclosed for testing compounds for use as anti-inflammatory drugs, inhibitors of amyloidogenesis, and/or inhibitors of tau protein pathology associated with Alzheimer's disease, in the treatment of a variety of neurological diseases.

11 Claims, 13 Drawing Sheets

OTHER PUBLICATIONS

Bullido, A polymorphism in the regulatory region of APOE associated with risk of Alzheimer's dementia, nature Genetics, Jan.–1998, vol. 18 69–71.

Das, Expression of the Alzheimer Amyloid–Promoting factor Antichymotrypsin is induces in human astrocytes by IL–1, Neuron, Feb. 1995, vol. 14 447–456.

Du, Association of an interleukin 1α polymorphism with Alzheimer's disease, Neurology, Aug. 2000, vol. 55 480–483.

Evans, Apolipoprotein E is a kinetic but not a thermodynamic inhibitor of amyloid formation: Implications for the pathogenesis and treatment of Alzheimer disease, Proc. Natl. Acad.Sci., Jan. 1995, vol. 92 763–767.

Fraser, $\alpha_1$–Antichymotrypsin binding to Alzheimer Aβ peptides is sequence specific and induces fibril disaggretation in vitro, Journal of Neurochemistry, 1993, vol. 61 (1) 298–305.

Games, Alzheimer–type neuropathology in transgenic mice overexpressing V717F β–amyloid precursor protein, Nature, Feb. 9, 1995, vol. 373 (9), 523–526.

Griffin, Brain interleukin 1 and S–100 immunoreactivity are elevated in Down syndrome and Alzheimer disease, Proc. Natl. Acad. Sci., Oct. 1989, voo. 86 7611–7615.

Grimaldi, Association of early–onset Alzheimer's Disease with an Interleukin–1α gene polymorphism, Ann Neurol 2000;47:361–365.

Haines, No genetic effect of $\alpha_1$Antichymotrypsin in Alzheimer's disease, Genomics, 1996, vol. 33 53–56.

Hill, Accelerated evolution in the reactive centre regions of serine protease inhibitors, Nature, Mar. 5, 1987, vol. 326 96–99.

Holtzman, Apolipoprotein E isoform–dependent amyloid deposition and neuritic degeneration in a mouse model of Alzheimer's disease, PNAS, Jan. 6, 2000, 1–6.

Hughes, $\alpha_2$–macroglobulin associates with β–amyloid peptide and prevents fibril formulation, Proc. Natl. Acad. Sci., Mar. 1998, vol. 95 3275–3280.

Hyman, Quantitative analysis of senile plaques in Alzheimer disease: Observation of log–normal size distribution and molecular epidemiology of differences associated with apolipoprotein E genotype and trisomy 21 (Down syndrome), Proc. Natl. Acad. Sci., Apr. 1995, vol. 92, 3586–3590.

Inglis, The murine Spi–2 proteinase inhibitor locus: a multigene family with a hypervariable reactive site domain, The EMBO Journal, 1991, vol. 10 (2), 255–261.

Janciauskiene, Alzheimer's peptide Aβ$_{1-42}$ binds to two β–sheets of $\alpha_1$–Antichymotrypsin and transforms it from inhibitor to subsrate, The Journal of biological chemistry, Oct. 23, 1998, vol. 273 (43) 28360–28364.

Eriksson, $\alpha_1$–Antichymotrypsin regulates Alzheimer β–amyloid peptide fibril formulation, Proc. Natl. Acad. Sci., Mar. 1995, vol. 92, 2313–2317.

Kamboh, APOE*4–associated Alzheimer's disease risk is modified by $\alpha_1$–Antichymotrypsin polymorphism, Nature Genetics, Aug. 1995, vol. 10 486–488.

Koo, Development expression of $\alpha_1$–Antichymotrypsin in brain may be related to Astrogliosis, Neurobiology of Aging, 1991, vol. 12 495–501.

Ma, Alzheimer Aβ neurotoxicity: promotion by Antichymotrypsin, ApoE4; inhibition by Aβ–related peptides, Neurobiology of Aging, 1996, vol. 17 (5) 773–780.

Ma, Amyloid–associated proteins $\alpha_1$–Antichymotrypsin and apolipoprotein E promote assembly of Alzheimer β–protein into filaments, Nature, Nov. 1994, vol. 372 (3) 92–93.

Mucke, Astroglial expression of human $\alpha_1$–Antichymotrypsin enhances Alzheimer–like pathology in amyloid protein precursor transgenic mice, American Journal of Pathology, Dec. 2000, vol. 157 (6), 2003–2009.

Muller, Lack of association between $\alpha_1$–Antichymotrypsin polymorphism, Alzheimer's disease, and allele E4 of apolipoprotein E, Neurology, Dec. 1996, vol. 47 1575–1577.

Nacmias, Implication of $\alpha_1$–Antichymotrypsin polymorphism in familial Alzheimer's disease, Neuroscience Letters, 1998, vol. 244 85–88.

Nakatani, An RNA polymerase II promoter containing sequences upstream and downstream from the RNA startpoint that direct initiation of transcription from the same site, Proc. Natl. Acad. Sci., Jun. 1990, vol. 87, 4289–4293.

Nicoll, Association of Interleukin–1 gene polymorphisms with Alzheimer's disease, Ann Neurol 2000; 47:365–368.

Nilsson, $\alpha_1$–Antichymotrypsin promotes β–sheet amyloid plaque deposition in a transgenic mouse model of Alzheimer's disease, The Journal of Neuroscience, Mar. 1, 2001, vol. 21 (5): 1444–1451.

Nilsson, The essential role of inflammation and induced gene expression in the pathogenic pathway of Alzheimer's disease, Frontiers in Bioscience, Apr. 16, 1998, vol. 3: 436–446.

Pasternack, Astrocytes in Alzeihmer's disease gray matter express $\alpha_1$–Antichymotrypsin mRNA, American Journal of Pathology, Nov. 1989, vol. 135 (5):827–834.

Potter, The involvement of proteases, protease inhibitors, and an Acute Phase Response in Alzheimer's disease, Annals of the New York Academy of Sciences, Dec. 31, 1992, vol. 674: 161–173.

Potter, The potential of BACE inhibitors for Alzheimer's therapy, Nature Biotechnoloby, Feb. 2000, vol. 18:125–126.

Rebeck, Apolipoprotein E in sporadic Alzheimer's disease: Allelic Variation and Receptor Interactions, Neuron, Oct. 1993, vol. 11: 575–580.

Rogers, Translation of the Alzheimer amyloid precursor protein mRNA is up–reglated by Interleukin–1 through 5'untranslated region sequences, The Journal of Biological Chemistry, Mar. 5, 1999, vol. 274 (10): 6421–6431.

Sanan, Apolipoprotein E associates with β amyloid peptide of Alzheimer's disease to form novel monofibrils, The American Society for Clinical Investigation, Inc, Aug. 1994, vol. 94: 860–869.

Sarid, Identification of a cis–acting positive regulatory element of the glial fibrillary acidic protein gene, Journal of neuroscience Research, 1991, vol. 28:217–228.

Schmechel, Increased amyloid β–peptide deposition in cerebral cortex as a consequence of apolipoprotein E genotype in late–onset Alzheimer disease, Proc. Natl. Acad. Sci., Oct. 1993, vol. 90: 9649–9653.

Sheng, S100β protein expression in Alzheimer disease: potential role in the pathogenesis of Neuritic plaques, Journal of Neuroscience Research, 1994, vol. 39;000–000.

Talbot, Polymorphism in AACT gene may lower age of onset of Alzheimer's disease, Neuroreport, Jan. 1996, vol. 7 (2):534–536.

Spillantini, Tau protein pathology in neurodegenerative diseases, TINS, 1998, vo. 21 (10):428–432.

Wisniewski, Acceleration of Alzheimer's Fibril formulation by apolipoprotein E in Vitro, American Journal of Pathology, Nov. 1994, vol. 145 (5):1030–1035.

Yoshiiwa, $\alpha_1$–Antichymotrypsin as a risk modifier for late–onset Alzheimer's disease in Japanese apolipoprotein E E4 Allele carriers, Ann Neurol, 1997, vol. 42:115–117.

Wisniewsk, Apolipoprotein E: A pathological chaperone protein in patients with cerebral and systemic amyloid, Neuroscience Letters, 1992, vol. 135: 235–238.

Yamada, Association of $\alpha_1$–Antichymotrypsin polymorphism with cerebral amyloid angiopathy, Ann Neurol, 1998, vol. 44:129–131.

Yamin, Metalloendopeptidase EC 3.4.24.15 is necessary for Alzheimer's amyloid–$\beta$ peptide degradation, The Journal of Biological Chemistry, Jun. 25, 1999, vol. 274 (26):18777–18784.

Janciauskiene, A specific structural interation of Alzheimer's peptide $A\beta_{1-42}$ with $\alpha_1$–antichymotrypsin, Nat. Struct. Biol., 1996, vol. 3(8):668–671.

McGeer, Anti–inflammatory drugs and Alzheimer disease, The Lancet, 1990, 335:1037.

* cited by examiner

High Power Magnification of (C)

64kDa−

100ng ACT
10 ng ACT
1ng ACT
8784
8783
8783
8782
non-transg.

GFAP/ACT mRNA−
GAPDH mRNA

Brain
Kidney
Liver
Heart
Spleen
Lung
Brain, non-transg.

ACT+/− mice

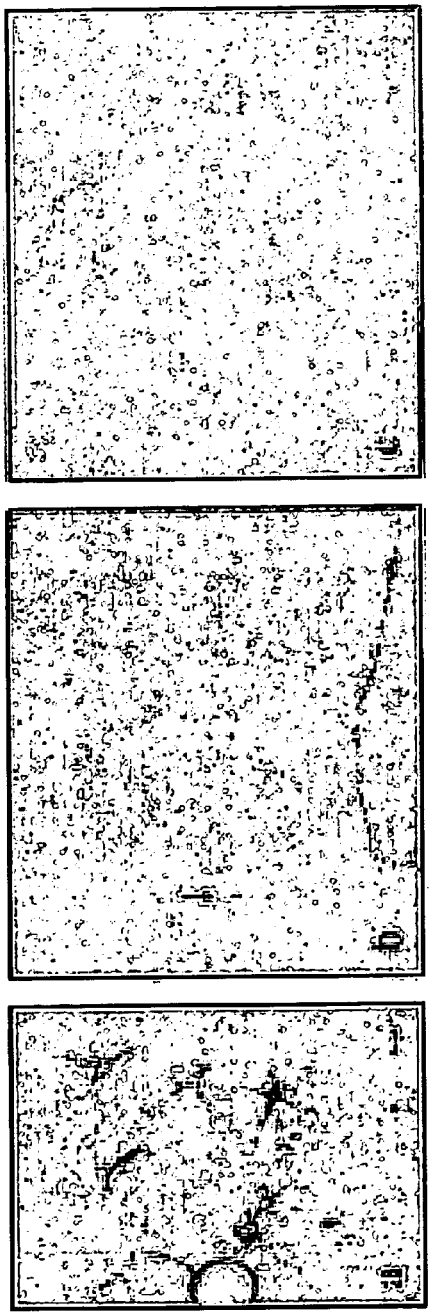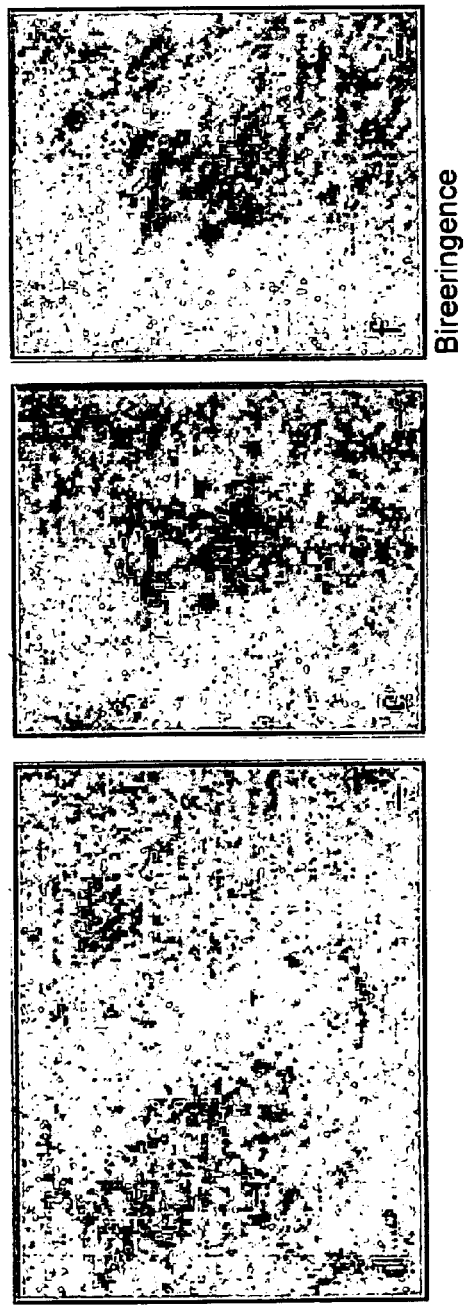

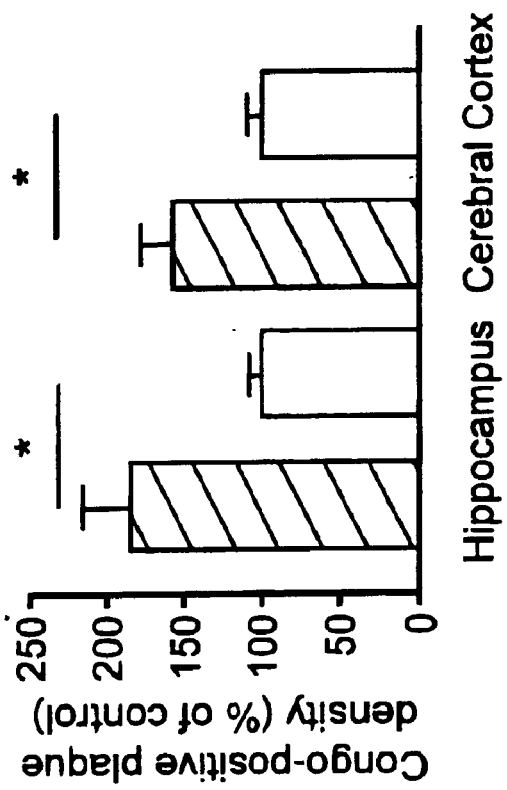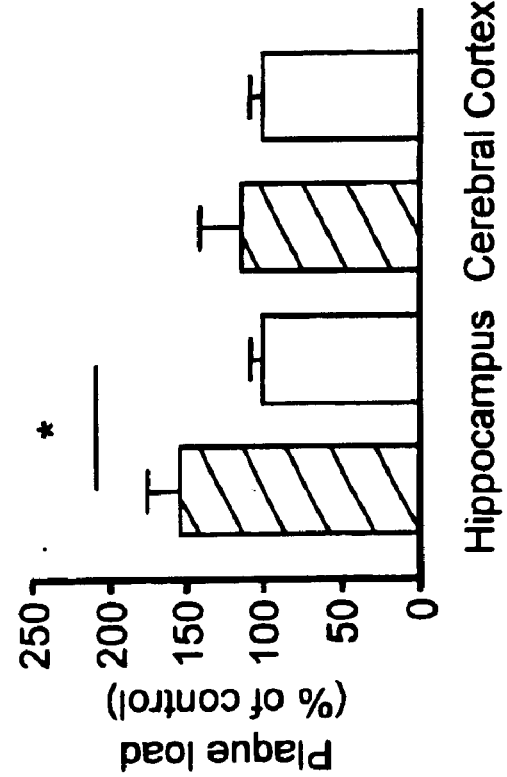

Hippocampus

Cerebral Cortex

FIG. 6A
FIG. 6B
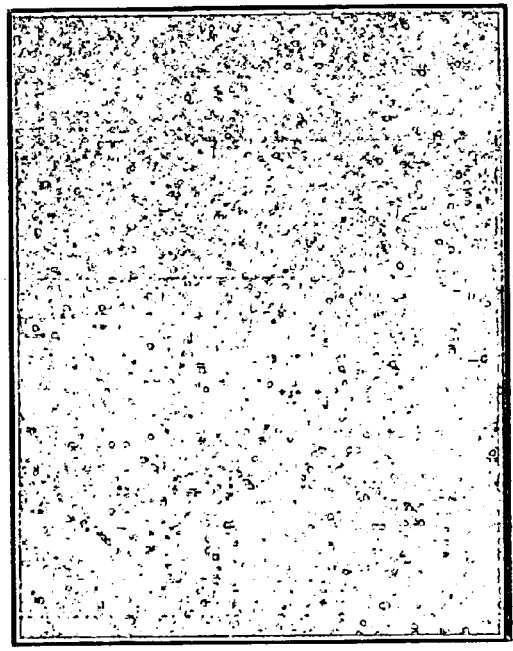
FIG. 6C

ACT #8783 transgenic mouse (CA1)

TRANSGENIC ANIMAL AND METHODS

PRIORITY

This application claims priority to Provisional U.S. Patent Application entitled, "Transgenic Animal and Methods," filed Jul. 13, 2000, having a Ser. No. 60/218,054, which is hereby incorporated in its entirety by reference.

SUPPORT

This invention was developed with support from the National Institute of Health, Grant No. AG09665, and the U.S. Government may therefore have certain rights in this invention.

1. FIELD OF THE INVENTION

This invention relates to a transgenic animal model of Alzheimer's disease and related neurological disorders in which the animal harbors a transgene encoding a protease inhibitor such as antichymotrypsin (ACT) protein. The invention further relates to transgenic animal models of Alzheimer's disease and related neurological disorders in which the animal harbors a transgene encoding a protease inhibitor such as antichymotrypsin (ACT) protein and one or more further transgenes affecting said neurological disorders. The invention further relates to cells comprising a transgene encoding an antichymotrypsin (ACT) protein. The invention also relates to drug screening assays using the invented transgenic cells or transgenic animals and progeny thereof.

2. BACKGROUND OF THE INVENTION

Biochemical, genetic, and epidemiological evidence indicates that inflammation is an essential part of the pathogenesis of Alzheimer's disease. For example, several acute phase/inflammatory molecules in the brain, specifically antichymotrypsin (ACT) and apolipoprotein E (apoE) can promote the formation of the neurotoxic amyloid deposits that are the main pathological hallmark of the disease. For further details and background information on Alzheimer's disease and related neurological diseases see, for example, U.S. Pat. Nos. 5,297,562; 6,043,283; 5,986,054; 5,981,208; 5,958,883; 5,854,215; 5,849,560; 5,830,670; 5,817,626; 5,773,220; 5,753,624; 5,731,284; 5,705,401; 5,571,671; 5,535,760; 5,506,097; 5,449,604; 5,434,170; 5,429,947; and 5,276,059 as incorporated herein by way of reference.

Amyloid plaque formation is found in a number of diseases including Alzheimer's Disease (AD), scrapie, bovine spongiform encephalopathy, Gerstmann-Straussler Syndrome and related transmissible spongiform encephalopathies (TSEs). These amyloid plaques comprise protein molecules bound together in a fibrinous matrix. Other disorders, such as Creutzfeldt-Jakob's disease, are characterized by the accumulation of amyloidogenic protein without deposition of amyloid plaques. Together these groups of conditions are referred to hereinafter as "Amyloidogenic Diseases." The present inventors were the first to discover that the acute phase protein, alpha1-antichymotrypsin (ACT) is a structural component of Alzheimer amyloid deposits. In vitro and in vivo studies have shown that the increased ACT expression in Alzheimer's disease is induced in astrocytes by the inflammatory cytokine IL-1 released from reactive microglial cells in the regions of amyloid deposition (Das, S. & Potter, H. "Expression of the Alzheimer amyloid-promoting factor antichymotrypsin is induced in human astrocytes by IL-1" Neuron 14:447–465,1995).

ACT is an inhibitor of chymotrypsin-like serine proteases and is normally produced in the liver as part of the body's "acute phase response" to inflammation. An important function of the acute phase response is to increase the general level of anti-protease activity in the body so as to reduce the potential damage that inflammation-associated proteases can inflict on normal serum proteins and healthy tissue outside of the immediate area of inflammation. The finding that ACT is overexpressed in astrocytes in affected areas of the Alzheimer brain provides the first clear indication that inflammation and an acute phase response in the brain are part of the disease. Other, independent, biochemical and epidemiological studies have confirmed the likelihood that these processes indeed play important roles in the pathogenesis of Alzheimer's disease. The important conclusion is that $A\beta$ does not act alone to cause Alzheimer's disease, but acts in concert with an inflammatory cascade, whose products are required for efficient amyloid formation.

The findings that ACT, together with the $A\beta$ peptide, is an integral component of the Alzheimer amyloid filaments, and that the mature amyloid deposits are restricted to the same brain regions in which ACT is overproduced, led to the proposal that ACT contributes directly to amyloid formation (Abraham, C. R., Selkoe, D. J. & Potter, H. "Immunohistochemical identification of the serine protease inhibitor $\alpha_1$-antichymotrypsin in the brain amyloid deposits of Alzheimer's disease" Cell 52:487–501,1990). When apolipoprotein E was found to be also present in Alzheimer amyloid, suggesting a similar role, the term "pathological chaperone" was coined to describe the potential function of these two, and possibly other proteins, in amyloid formation (Wisniewski, T. & Frangione, B. "Apolipoprotein E: a pathological chaperone protein in patients with cerebral and systemic amyloid" Neurosci. Lett. 135:235–238, 1992). Indeed, when ACT or apoE are added to preparations of synthetic $A\beta$ peptide in vitro, they promote the polymerization of $A\beta$ into amyloid filaments (Ma, J., Yee, A. Brewer, H. B. Jr. & Das, J. & Potter, H. "Amyloid-associated proteins $\alpha_1$-antichymotrypsin and apolipoprotein E promote assembly of Alzheimer's $\beta$-protein into filament" Nature 372:92–94, 1994; Wisniewski, T., Castano, E. M., Golabek, A., Vogel, T. & Frangione, B. "Acceleration of Alzheimer's fibril formation by apolipoprotein E in vitro" Am. J. Pathol. 145:1030–1035, 1994; Sanan, D. A., Weisgraber, K. H., Russell, S. J., Mahley, R. W., Huang, D., Saunders, A., Schmechel, D., Wisniewski, T., Frangione, B., Roses, A. D. & Strittmatter, W. J. "Apolipoprotein E associates with beta amyloid peptide of Alzheimer's disease to form novel monofibrils. Isoform apoE4 associates more efficiently than apoE3" J. Clin. Invest. 94:860–869, 1994). ApoE4, the isoform of apoE, identified by epidemiological studies as a strong risk factor for inherited Alzheimer's disease (Strittmatter, W. et. al. "Apolipoprotein E: high avidity binding to $\beta$-amyloid and increased frequency of type 4 allele in late-onset familial Alzheimer's disease" Proc Natl Acad Sci USA 90, 1977–1981, 1993; Corder, E. et. al. "Gene dose of apolipoprotein E type 4 allele and the risk of Alzheimer's disease in late onset families" Science 261, 921–923, 1993), is a much more active amyloid promoting factor than the non-pathogenic apoE3 or apoE2 isoforms. Furthermore, the greater number and length of the filaments formed under the promoting effect of ACT and apoE4 show increased toxicity to human cortical neurons in culture (Ma, J., Brewer, H. B. Jr., & Potter, H. "Alzheimer A beta neurotoxicity: promotion by antichymotrypsin. ApoE4; inhibition by A beta-related peptides." Neurobiol Aging 17:773–78, 1996). Together, these results support the hypothesis that Alzheimer's disease involves an inflammation-like reaction and a consequent acute phase response in the brain that is essential for the development of mature amyloid neuropathology and neuronal cell death.

Since demonstration that ACT and apoE, especially apoE4, are amyloid promoters in vitro, many other proteins have been tested for their possible effect on Aβ polymerization, such as amyloid P component, acetylcholinesterase and complement factors (for review see Nilsson, L., Rogers, J. & Potter, H. "The essential role of inflammation and induced gene expression in the pathogenic pathway of Alzheimer's disease" Front. Biosci. 16:426–446, 1998). ACT and apoE are the only such molecules for which genetic studies support their involvement in the Alzheimer pathogenic pathway. For example, one of the greatest genetic risk factors for developing Alzheimer's disease is the inheritance of one, or worse, two copies of the apoE4 allele. Furthermore, inheritance of apoE leads to increased numbers of amyloid deposits in both Alzheimer patients and normal aged individuals, suggesting that apoE plays a direct role in amyloid formation, rather than, for instance increasing cells' sensitivity to neurotoxicity.

Genetic support for the involvement of ACT in Alzheimer's disease has been not so obvious as for apoE4. In one study, the inheritance of a specific isoform of ACT (an alanine instead of a threonine in the signal peptide) correlated with a 8-fold increased risk of developing Alzheimer's disease in apoE4 carriers (Kamboh, M. I., Sanghera, D. K., Ferrell, R. E. & DeKosky, S. T. "ApoE4-associated Alzheimer's disease risk is modified by $\alpha_1$-antichymotrypsin polymorphism" Nature Genet. 10:486–488, 1995). Since this single amino acid change does not affect the secreted protein itself and therefore cannot alter its affinity for the Aβ peptide or its ability to promote Aβ polymerization, it is possible that the effect is on the synthesis and secretion of the ACT protein. This result has been confirmed and modified by several others (Thome, J., Baumer, A., Kornhuber, J., Rosler, M., and Riederer, P. "Alpha-1-antichymotrypsin bi-allele polymorphism, apolipoprotein E tri-allele polymorphism and genetic risk of Alzheimer's syndrome" J. Neural Trans. 10:207–212, 1995; Morgan et al.; 1996; Talbot, C., Houlden, H., Craddock, N., Crook, R., Hutton, M., Lendon, C., Prihar, G., Morris, J. C., Hardy, J. & Goate, A. "Polymorphisms in AACT gene may lower age of onset of Alzheimer's disease" Neuroreport. 7:534–536, 1996). Most recently, a study showed that inheritance of the ACT-A allele (independent of apoE alleles) was highly correlated to the extent of amyloid angiopathy in the brain (Yamada, M., Sodeyma, N., Itoh, Y., Suematsu, N., Otomo, E., Matsushita, M. & Mizusawa, H. "Association of the alpha1-antichymotrypsin polymorphism with cerebral amyloid angiopathy" Ann. Neurol. 44:129–131, 1998).

Although the pathological evidence (such as the overexpression of ACT in affected areas of AD brain and the increased amyloid load in apoE4 and ACT-A carriers) and much of the biochemical evidence, has pointed to such proteins being amyloid promoters, it is also possible from the genetic data alone that, for instance, apoE can be an amyloid inhibitor with apoE4 being a less effective inhibitor than apoE3. Indeed, there exist in vitro studies in which apoE or ACT appeared to inhibit Aβ polymerization (see, for example, Evans, K. C., Berger, E. P., Cho, C-G, Weisgraber, K. H. & Lansbury, P. T. Jr. "Apolipoprotein E is a kinetic but not a thermodynamic inhibitor of amyloid formation: implications for the pathogenesis and treatment of Alzheimer's disease" Proc. Natl. Acad. Sci. U.S.A. 92:763–767, 1995; Eriksson, S., Janciauskiene, S. & Lannfelt, L. "$\alpha_1$-antichymotrypsin regulates Alzheimer β-amyloid peptide fibril formation" Proc. Natl. Acad. Sci. U.S.A. 92:2313–2317, 1995; Fraser, P. E., Nguyen, J. T., McLachlen, D. R., Abraham, C. R. & Kirschner, D. A. "$\alpha_1$-antichymotrypsin binding to Alzheimer Aβ peptides is sequence specific and induces fibril disaggregation in vitro" J. Neurochem. 61:298–305, 1994). The further confusion for the role apoe has recently been provided by a series of in vivo experiments that show it to be an amyloid promoter (Bales, K. R.; Verina, T., Dodel, R. C., Du, Y., Altstiel, L., Bender, M., Hyslop, P., Johnstone, E. M., Little, S. P., Cummins, D. J., Piccardo, P., Ghetti, B. & Paul, S. M. "Lack of apoliprotein E dramatically reduces amyloid β-peptide deposition" Nature Genet. 17:263–264, 1997). Specifically, a set of mouse strains were developed that expressed transgenic human APP but which had their apoE gene either half (heterozygous) or completely (homozygous) knocked out. The animals showed a variable amount and speed of amyloid deposition that was absolutely dose-dependent on the number of copies of the apoE gene. If there was no apoE, mature, filamentous amyloid did not form in animals up to two years of age, compared to massive amyloid deposition by 7 months in the presence of the normal two copies of the apoE gene (Bales et al., 1997, supra). One copy of apoE gave intermediate results. It therefore appears that human Aβ, by itself, is incapable of forming amyloid in the mouse without the promoting effect of apoE. Therefore, the current state of the art is still contradictory as there are studies supporting two opposite roles for ACT and other amyloid plaque-associated factors.

If APP mice lacking apoE fail to form amyloid filaments, one might ask whether ACT still has a role to play in amyloid formation, or whether apoE is sufficient. However, such a study is complicated by the fact that mice do not have an ACT gene per se. The closest mouse homologue is contrapsin which is quite different from ACT. Contrapsin does not bind Aβ, and is not expressed in the same way as ACT. Therefore, apoE may be the only, or most important amyloid promoter in mice, but ACT remains a candidate for a similar function in humans. It would be desirable, therefore, in the field of the present invention, to study the amyloid-promoting and/or suppressing effect of ACT, under in vitro conditions to correctly identify its role as an amyloid promoter/inhibitor.

The defining pathological characteristics of Alzheimer's disease are plaques, tangles, inflammation, and neuronal degeneration. However, very little is known about the mechanism by which tangles and their component paired helical filaments form and the precise relationship between neuronal degeneration and the other pathological features of AD. It is clear that post-translationally modified microtubule associated protein tau is the major PHF protein, but what induces the modifications such as hyperphosphorylation of certain amino acids in AD is unknown. It has been particularly irksome that the best transgenic models of AD expressing mutant human genes that cause inherited AD form plaques and exhibit inflammation but do not develop tangles or neuronal cell death. It would therefore be advantageous for an animal model of Alzheimer's disease to exhibit Tau protein pathology found in the human disease, including hyperphosporylated Tau, paired helical filaments, neurofibrillary tangles and neuronal degeneration.

Several prior unsuccessful attempts have been made to generate transgenic mice expressing ACT. In a first attempt in 1989 by the present inventors, the ACT coding region was linked to the SV40 promoter for driving expression in all tissues, since no astrocyte-specific promoters had yet been characterized. Unfortunately, general expression of this protease inhibitor resulted in the animals dying within a week of birth.

A second attempt to generate ACT mice was performed in which the glial fibrillary acidic protein (GFAP) promoter was used. However, no ACT protein expression occurred in the brains of the animals, even after a stab wound was used to induce gliosis (Mucke et al. 2000 American Journal of Pathology 157:2003–2010).

Accordingly, it is desirable to provide in the field of the present invention, a transgenic animal and cells derived therefrom, which is useful as a model for Alzheimer's disease and related neurological diseases, and which preferably expresses ACT within the brain of the animal. Such a transgenic animal and cells would be desirable in the study and development of therapeutic approaches toward the treatment and management of such neurological diseases. For example, such transgenic animal and cells would be advantageous in the screening of compounds for the treatment and management of Alzheimer and related neurological diseases. These advantages and more will be apparent to one of ordinary skill in the art upon reading the following disclosure and examples.

3. SUMMARY OF THE INVENTION

It is therefore a feature and advantage of the present invention to provide a transgenic mammal, preferably a mouse, which serves as a model for Alzheimer's disease and related neurological disorders having a pathology comprising amyloid plaque formation. This transgenic animal carries an exogenous polynucleotide which has a coding sequence functionally equivalent of the DNA sequence of a protease inhibitor such as, for example, human antichymotrypsin (ACT), together with DNA sequences directing its expression, preferably a glial fibrillary acidic protein (GFAP) promoter and 5'0 UTR, most preferably modified to remove ATG start codons from its sequence. The mammalian polynucleotide can be in the form of DNA, genomic DNA, cDNA, mRNA and various fragments and portions of the gene sequence encoding ACT. Accordingly, the transgenic mouse exhibits one or more of the symptoms of cognitive memory loss and/or behavioral disturbances, amyloid accumulation, neuronal cell death or synapse loss, formation or aggregation of abnormal protein filaments, or phosphorylation of one or more proteins related to Alzheimer's disease such as tau. In addition or alternatively, the symptoms can appear as another cellular tissue disorder such as in mouse liver, kidney, spleen, bone marrow or other organs in which the human ACT gene product is expressed.

According to the second embodiment of the invention, animals, primary cell cultures, and cell lines are provided which derive from the parent transgenic animal carrying ACT gene. Accordingly these descendant animals, primary cell cultures and cell lines, which are defined hereinafter as a "progeny", are either homozygous or heterozygous for ACT allele.

Accordingly, in another embodiment, the transgenic ACT animal expresses one or more additional transgenes of proteins whose expression may be associated with Alzheimer's disease or related neurological disorders, where the second transgene encodes a normal, mutant, or altered gene encoding, for example, tau-1, apolipoprotein E, APP, presenilin 1, presenilin 2, IL-1 alpha, or IL-1 beta.

As another embodiment of the invention a screening method is provided wherein various test compounds are screened using transgenic animals and/or progeny of the invention. Compounds that are found to have an effect on ACT expression, or to promote or inhibit any of the diverse biochemical effects of ACT expression, are then further tested and used in treatment of Alzheimer's disease and/or related neurological disorders. In accordance with another aspect of the invention, progeny of the invention can be used as starting points for rational drug design to provide ligands, therapeutic drugs or other types of small chemical molecules. Alternatively, small molecules or other compounds identified by the above-described screening assays can serve as "lead compounds" in rational drug design.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

4. BRIEF DESCRIPTION OF FIGURES

FIG. 1 Illustrates expression of human ACT; Left panel shows Northern blot hybridization with an ACT probe of polyA+ mRNA from (lane 1) untransfected and (lane 2) GFAP-HACT DNA, and (lane 3) untreated and (lane 4) IL-1 treated U373 MG human astrocytoma cells showing the position of the native human ACT transcript (which is slightly smaller than the fusion gene transcript); Two Right Panels show Immunoprecipitation/Western blot showing ACT protein in (lane 1–2) transfected, (lanes 3–4) untransfected C6 glioma cells. Untransfected cell spiked with 10 pg and 1 ng respectively of human ACT are shown in lanes 5, 6. Lanes 7 and 8 (and a shorter exposure of lanes 9 and 10) show cells transfected with a CMV-ACT construct which expresses ACT at high levels.

FIGS. 2A–F illustrates expression of ACT mRNA and protein in ACT transgenic mice. Immunoprecipitation/Western blot of brain protein extracts from a non-transgenic mouse and ACT-transgenic founder lines (#8782, #8783 and #8784) displaying a protein band (~68 kDa) that comigrates with human serum ACT (a). GFAP/ACT-mRNA and GAPDH-mRNA expression in brain of non-transgenic mouse and various tissues of heterozygous ACT-transgenic mouse (b). Colocalization of ACT (brown) and GFAP (blue)-immunoreactivity in astrocytes of ACT$^{+/-}$-mice (c). Profound astrocyte expression and secretion of ACT-immunoreactivity in the hippocampal formation of heterozygous ACT-transgenic mice (d) but absence of ACT-immunostaining in non-transgenic mouse (e) 3 days after stab wound injury. Sections were counterstained with Methyl Green (d and e).

FIGS. 3A–F Illustrates astrocyte-specific expression and plaque association of ACT protein in ACT transgenic mice. ACT-immunopositive astrocytes in a 10 months old PDGF-hAPP(V717F)$^{+/-}$, ACT$^{+/-}$-mice (a), but absence of immunostaining in a 10 month old PDGF-hAPP(V717F)$^{+/-}$-ACT$^{+/-}$-mice (b). The astrogliotic ACT-immunostaining was clearly visible along the hippocampal fissure in 6 months old mice (c). High-power magnification of ACT-immunopositive Congo-positive amyloid plaque in a PDGF-hAPP(V717F)$^{+/-}$, ACT$^{+/-}$-m-ice at 10 months of age (d), displaying birefringence under polarized light (e).

FIG. 4 Illustrates increased plaque load and density in APP/ACT transgenic mice. Increased total Congo-positive amyloid load (a) and numerical plaque density (b) in the hippocampus as well as the cerebral cortex of 10 months old PDGF-hAPP(V717F)$^{+/-}$, ACT$^{+/-}$-mice (n=7, solid bar), as compared to age-matched PDGF-hAPP(V717F)$^{+/-}$, ACT$^{-/-}$-mice (n=6, open bar).

FIG. 5 Illustrates plaque density analysis. Numbers of plaques in the hippocampus (a) and the cerebral cortex(b) were stratified for plaque size. Relative frequency histograms of plaque size distribution in mice of the PDGF-hAPP(V717F)$^{+/-}$, ACT$^{+/-}$ (solid bar) and the PDGF-hAPP(V717F)$^{+/-}$, ACT$^{-/-}$-genotypes (hatched bar) in the hippocampus (c) and the cerebral cortex (d). Superimposed is the best-fit to a Gaussian distribution in mice of the PDGF-hAPP(V717F)$^{+/-}$, ACT$^{+/-}$ (solid lines) and the PDGF-hAPP(V717F)$^{+/-}$, ACT$^{-/-}$-genotypes (broken line). The results displayed are expressed as percentage of the control group (the PDGF-hAPP(V717F)$^{+/-}$, ACT$^{-/-}$-genotype) and represent mean±s.e.m.

FIG. 6 Illustrates ACT-immunostaining of the hippocampus of (a) ACT founder line 8783, (b) 8784, and (c) a non-transgenic control mouse.

5. DETAILED DESCRIPTION OF THE INVENTION

Figure 1:
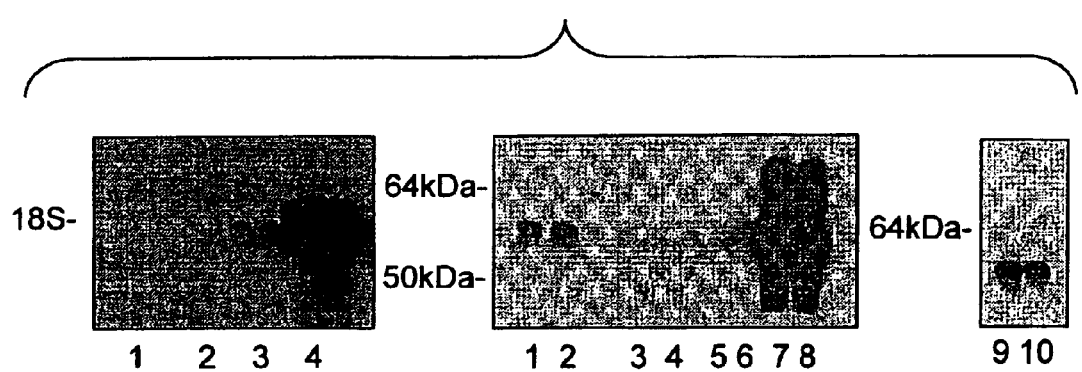

The following definitions may be useful in comprehending the disclosure of the present invention.

Nucleic acid: refers to a deoxyribonucleotide or ribonucleotide polymer in either single- or double-stranded form, and unless otherwise limited, would encompass analogs of natural nucleotide that can function in a similar manner as naturally occurring nucleotide. Nucleic acids may be cloned or synthesized using any technique known in the art. They may also include non-naturally occurring nucleotide analogs, such as those which are modified to improve hybridization and peptide nucleic acids.

Transgenic: DNA can be introduced into a murine embryo during embryo genesis by injection into the nucleus of a fertilized egg using an injection needle. In this case, the gene of interest may be directly injected into the nucleus (particularly, pronucleus) of a fertilized egg, or alternatively transgenes carrying sequences such as suitable transcriptional control region (containing, for example, enhancer, GFAP promoter, silencer and the like) and poly A addition signal, the sequences being necessary for proper expression of the genes of interest on the murine genome, may be prepared and then injected into the nucleus of a fertilized egg. Injection can be performed using a microinjector, micromanipulator, or the like, preferably microinjector due to good efficiency of gene transfer and good operability. The genes of interest can be introduced into a fertilized egg separately or concurrently, preferably concurrently because time needed for introduction becomes shorter due to only one manipulation of introduction, and because the fertilized egg has less damage.

Transgene: as used herein refers to a construct for introducing into the murine genome to prepare a transgenic mouse, the construct comprising a DNA sequence of a gene of interest to be introduced. The transgene according to the present invention may be linear or circular, preferably linear in view of the efficiency of integration in the chromosome of a mouse.

Transgenic animal: is any animal, preferably a non-human mammal in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of the subject ACT protein. Preferred non-human animals are selected from the rodent family including rat and mouse, most preferably mouse.

Promoter: as used herein refers to DNA capable of acting as a promoter (i.e., having promoter function). The term "promoter" as used herein refers to a specific nucleotide sequence on DNA, which initiates the synthesis of mRNA (i.e., transcription) with the DNA as a template. The promoter has a common sequence of nucleotides, and RNA polymerase recognizes the nucleotide sequence and synthesizes mRNA. The term "promoter function" as used herein refers to a function that RNA polymerase binds to a specific region on DNA and initiates the transcription.

Tau proteins: without being limited by theory, it is believed now that, in Alzheimer's disease, the amyloid beta-protein is accumulated in the neurons and that, as a result of its correlation with the formation of PHF, death of the neurons results. It has been known that the tau proteins, e.g., tau-i is usually a series of related proteins forming several bands at the molecular weights of 48–65 kd on SDS polyacrylamide gel electrophoresis and that it promotes the formation of microtubules. It is known that the tau which is incorporated in the PHF of the brain of Alzheimer's disease is hyperphosphorylated compared to normal tau.

Normal, mutant, or altered gene: It is also possible to modify the structure of the subject protease inhibitor protein for such purposes as enhancing or decreasing biological or pathological activities, or to facilitate screening methods for compounds that modulate their activity. Such modified polypeptides, expressed from a mutant or altered gene when designed to retain at least one activity of the naturally-occurring form of the protein, are considered functional equivalents of the protease inhibitor proteins described in more detail herein. Such modified polypeptides can be produced, for instance, by amino acid substitution, deletion, or addition, for which corresponding base substitutions or deletions within the normal, mutant, or altered gene are required. It is reasonable to expect, for example, that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide= asparagine, glutamine; and (6) sulfur-containing=cysteine and methionine. (see, for example, Biochemistry, 2 nd ed, Ed. by L. Stryer, W H Freeman and Co.: 1981). Whether a change in the amino acid sequence of a peptide results in a functional homolog can be readily determined by assessing the ability of the variant peptide to produce a response in cells in a fashion similar to the wild-type protein. For instance, such variant forms of ACT can be assessed for their ability to induce the pathological effects described herein. Peptides in which more than one replacement has taken place can readily be tested in the same manner.

Amyloidosis: is art recognized and is intended to include amyloid deposition related symptoms, such as progressive and undesirable memory impairment, loss of language and visuospatial skills, and behavior deficits. These changes in cognitive function are the result of degeneration of neurons in the cerebral cortex, hippocampus, basal forebrain, and other regions of the brain. The presence of large numbers of neurofibrillary tangles in degenerated neurons, neuritic plaques in the extracellular space and in the walls of the cerebral microvasculature are a result of amyloid deposition. For example, neuritic plaques which consist of deposits of proteinaceous material surrounding an amyloid core.

A person "suffering from AD" is a person who has been diagnosed as having AD, by a practitioner of at least ordinary skill in the art of clinically diagnosing (e.g., diagnosing in patients antemortem) AD, using methods and routines, such as those described above, that are standard in the art of such clinical diagnoses. The invention entails treating AD in persons suffering therefrom and preventing AD in persons susceptible thereto.

By "treating AD" is meant slowing or preventing the progression or worsening of the disease that is now known to occur when the disease is untreated.

Many proteins have been found that change their phosphorylation state (i.e. become phosphorylated or dephosphorylated) as a result of Alzheimer's disease. Such proteins include, but are not limited to, APP, cdc-2/cyclin B, cdk5, p53, cdc47, MAD, cyclin D, or cyclin E.

Many proteins have been found that either make onset of Alzheimer's disease more likely or faster. Such proteins are of great interest and are known to those of skill in the art. These proteins include, but are not limited to tau-I, apolipoprotein E, APP, presenilin 1, presenilin 2, IL-1 alpha, or IL-1 beta.

The preferred promoter of the present invention is GFAP, but it should be noted that other promoters that are capable of directing protein expression in the brain and optionally in other tissues from an operably attached transgene are suitable for use in the present invention. Most preferably, the GFAP promoter is modified to remove undesired ATG start codons located upstream from the ATG start codon of the desired transgene within the construct.

By "monitoring a pathological marker" is meant any measurement that is responsive to any of the known pathological markers recognized in the art as consistent with Alzheimer's disease, including, but not limited to, plaques, tangles, PFT, synapse loss, neuronal death, elevated or decreased levels of diagnostic proteins including A-beta peptides, and the like. For example, neuronal cell death or synapse loss may conveniently be measured by TUNEL staining, neurofilament antibody staining, or synaptophysin antibody staining.

One puzzle relating to Alzheimer's disease is that the major amyloid component—the Aβ peptide—is expressed throughout the body and the brain in both normal and Alzheimer individuals, and yet deposits as mature amyloid only in specific regions of the Alzheimer brain. The identification of ACT and apoE4 as amyloid-associated proteins and as amyloid-promoting factors, provides a mechanism for the region-specific and disease-specific deposition of amyloid. The present inventors have discovered that (1) ACT is overexpressed only in areas of Alzheimer-affected brain showing mature amyloid neuropathology; (2) that ACT is expressed in astrocytes in response to IL-1; and (3) that IL-1-expressing microglia cells are only present in Alzheimer's brain in areas showing neuropathology and ACT overexpression, suggest that the reason that Alzheimer amyloid neuropathology develops only in certain brain regions, may, in part, be due to the region-specific inflammatory cascade that leads to expression of the amyloid promoting factor ACT as an early step in the Alzheimer pathogenic pathway (Das and Potter, 1995).

The present invention derives from an unexpected appreciation that the mRNA start site in GFAP is more upstream than previously thought, and the consequent removal by site-directed mutagenesis of several potentially confounding ATG codons in the 5'UTR of GFAP greatly increases the levels of ACT mRNA and protein expression in transfected glioblastoma cells. Based on this insight, the present inventors have generated a transgenic mouse line containing a cDNA fusion-construct with a 6 kbp mouse GFAP promoter and 200 bp of the 5'-end of the GFAP attached to the human ACT cDNA clone. In addition, several ATG start codons in the GFAP part of the transcript that previously interfered with ACT expression have been deleted and the human ACT gene placed downstream of the GFAP transcription start site. The non-coding 3'UTR of the mRNA is derived from the rat preproinsulin II gene, which provides a 3' intronic region and a polyadenylation (polya) site.

As a first test of function, the GFAP-ACT construct is assayed for its ability to support ACT mRNA and protein expression after transient transfection into C6 glioma cells. This cell-line is selected because of its rat origin and which allows the human ACT mRNA and protein to be easily distinguished from any rat species. The summary of results is shown in FIG. 1.

Transgenic mice (FVB/N strain) are then generated using the GFAP/ACT expression plasmid and conventional oocyte injection. PCR is used to confirm the presence of the complete transgene in three founder animals and to show that the transgene is passed intact to half of the progeny of these founders mated with wild type mice. Select animals of the heterozygous offspring are then inbred to generate homozygous transgenic animals. The successful expression of human ACT in the brains of several heterozygous transgenic ACT mice, but not in wild type mice, is demonstrated using non-radioactive Immunoprecipitation/Western blots (see FIG. 2). The major band comigrates with ACT purified from human serum, indicating that the mice not only express human ACT, but also correctly glycosylate it.

The ACT mice and/or the progeny of their crossing with other mice develop Alzheimer-like pathology such as amyloid deposits, neurofibrillary tangles, synapse loss, and neuronal degeneration and do develop behavioral and memory deficits. For example, the human ACT transgenic mice are also mated with transgenic mouse strains that express an Alzheimer's disease mutated form of the human APP gene (PDGF-APP), and which as a result produce numerous congophilic plagues (Congo stain positive) in the hippocampus and cortex. It is known that brain tissue from Alzheimer's disease (AD) patients contained amyloid plaques which are stainable with Congo Red. The additional presence of an expressed ACT gene in the progeny of this cross increases the rate or extent of amyloid formation and of the development of other Alzheimer-like pathology.

Recent results of mating the PDGF-APP mice to apoE knockout mice have indicated that apoE is essential for amyloid formation (Bales et al., 1997). These APP/apoE KO mice are mated to the ACT transgenics to determine whether and how ACT and apoE interact to promote amyloid formation. For example, in the APP+/+ apoE−/− mice, no amyloid develops up to two years of age. When ACT expression is introduced into this background, amyloid deposition occurs. One or two copies of apoE contribute a dose-dependent optimal amyloid promoting effect. The various strains are also useful for studies of relative behavior changes.

It is thus clear that this invention is not limited to ACT mice only but also to any progeny of mating the ACT mice to other mice such that the progeny express human ACT in the brain. The resulting mice are equally important for studies of Alzheimer and other related Amyloidogenic Diseases.

In addition to Alzheimer's Disease (AD), a large number of related "amyloidogenic diseases" are contemplated, including but not limited to scrapie, transmissible spongioform encephalopathies (TSE's), hereditary cerebral hemorrhage with amyloidosis Icelandic-type (HCHWA-I), hereditary cerebral hemorrhage with amyloidosis Dutch-type (HCHWA-D), Familial Mediterranean Fever, Familial amyloid nephropathy with urticaria and deafness (Muckle-Wells syndrome), myeloma or macroglobulinernia-associated idopathy associated with amyloid, Familial amyloid polyneuropathy (Portuguese), Familial amyloid cardiomyopathy (Danish), Systemic senile amyloidosis, Familial amyloid polyneuropathy (Iowa), Familial amyloidosis (Finnish), Gerstmann-Staussler-Scheinker syndrome, Medullary carcinoma of thyroid, Isolated atrial amyloid, Islets of Langerhans, Diabetes type II, and Insulinoma. Many of these conditions are associated with deposition of amyloid plaques.

In a preferred form of the invention, the method of using instant mice is contemplated which is eventually useful for treating, preventing and/or inhibiting conditions associating with plaques occurring in a tissue of the central nervous system of said animals. In another form, the method useful against a disease of the internal organs related to amyloid plaque formation, including plaques in the heart, liver, spleen, kidney, pancreas, brain, lungs and muscles.

In a preferred embodiment, the present invention provides assays for identifying small molecules or other compounds which are capable of inducing or inhibiting the expression of ACT other ACT-related genes and proteins. The assays can be performed in vitro using non-transformed cells, immortalized cell lines, or recombinant cell lines expressing ACT. Specifically the assays are designed in a such a way as to detect the presence of increased or decreased expression of ACT or other inflammatory genes or proteins acting in concert with ACT. These comprise assays to measure increased or decreased mRNA expression (using, e.g., the nucleic acid probes), increased or decreased levels of ACT or other ACT-related protein products (using, e.g., the anti-ACT antibodies produced by art-known methods), or increased or decreased levels of expression of a reporter gene (e.g., beta-galactosidase or luciferase) operatively joined to ACT 5' regulatory region in a recombinant construct.

Thus, for example, one can culture cells known to express the ACT and add to the culture medium one or more test compounds. After allowing a sufficient period of time (e.g., 6–72 hours) for the compound to induce or inhibit the expression of the ACT, any change in levels of expression from an established baseline is detected using any of the techniques described above and well known in the art. In particularly preferred embodiments, the cells are from an immortalized cell line such as a human glioblastoma cell line or an astrocyte cell line. Using the nucleic acid probes and/or antibodies disclosed and herein, detection of changes in the expression of ACT, and thus identification of the compound as an inducer or repressor of ACT expression, requires only routine experimentation.

In particularly preferred embodiments, a recombinant assay is employed in which a reporter gene such as β-galactosidase or luciferase is operably joined to the 5' regulatory regions of ACT gene. Such regulatory regions are easily isolated and cloned by one of ordinary skill in the art in light of the present disclosure of the coding regions of these genes. The reporter gene and regulatory regions are joined so that transcription and translation of the reporter gene may proceed under the control of the ACT regulatory elements. The recombinant construct is then introduced into any appropriate cell type although mammalian cells are preferred. The transformed cells are grown in culture and, after establishing the baseline level of expression of the reporter gene, test compounds are added to the medium. The ease of detection of the expression of the reporter gene provides for a rapid, high throughput assay for the identification of inducers and repressors of ACT gene.

Compounds identified by this method will have the utility in modifying the expression of ACT and other inflammatory genes in vivo. These compounds are then further tested in the animal models disclosed and enabled herein to identify those compounds having the most potent in vivo effects. In addition, as described above with respect to small molecules having ACT-binding activity, these molecules can serve as "lead compounds" for the further development of pharmaceuticals by, for example, subjecting the compounds to sequential modifications, molecular modeling, and other routine procedures employed in rational drug design.

Thus, the present invention also contemplates therapeutic compounds preferably in a pharmaceutically acceptable carrier or diluent.

With respect to in vivo applications, the compounds identified by above screening methods can be administered to a patient in a variety of ways including, for example, parenterally, orally or intraperitoneally. Parenteral administration includes administration by the following routes: intravenous, intramuscular, interstitial, intraarterial, subcutaneous, intraocular, intrasynovial, transepithelial, including transdermal, pulmonary via inhalation, opthalmic, sublingual and buccal, topical, including ophthalmic, dermal, ocular, rectal, and nasal inhalation via insufflation or nebulization.

The compounds are preferably orally administered, for example, with an inert diluent or with an assimilable edible carrier, they can be enclosed in hard or soft shell gelatin capsules, or they can be compressed into tablets. For oral therapeutic administration, the active compounds can be incorporated with an excipient and used in the form of ingestible tablets, buccal tablets, troches, capsules, sachets, lozenges, elixirs, suspensions, syrups, wafers, and the like. The pharmaceutical composition comprising the active compounds can be in the form of a powder or granule, a solution or suspension in an aqueous liquid or non-aqueous liquid, or in an oil-in-water or water-in-oil emulsion.

The tablets, troches, pills, capsules and the like can also contain, for example, a binder, such as gum tragacanth, acacia, corn starch or gelating, excipients, such as dicalcium phosphate, a disintegrating agent, such as corn starch, potato starch, alginic acid and the like, a lubricant, such as magnesium stearate, and a sweetening agent, such as sucrose, lactose or saccharin, or a flavoring agent. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring. Any material used in preparing any dosage unit form should be pharmaceutically pure and substantially non-toxic. In addition, the active compound can be incorporated into sustained-release preparations and formulations.

The active compounds can be administered parenterally or intraperitoneally. Solutions of the compound as a free base or a pharmaceutically acceptable salt can be prepared in water mixed with a suitable surfactant, such as hydroxypropylcellulose. Dispersions can also be prepared in glycerol, liquid polyethylene glycols, and mixtures thereof, and in oils. Under ordinary conditions of storage and use, these preparations can contain a preservative and/or antioxidants to prevent the growth of microorganisms or chemical degeneration.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It can be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and any of the other ingredients from those enumerated above. In the case of sterile powders for the preparation of sterile injectable solutions, the preferred methods of preparation are vacuum drying and the freeze drying technique.

Pharmaceutical compositions which are suitable for administration to the nose or buccal cavity include powder, self-propelling and spray formulations, such as aerosols, atomizers and nebulizers.

The therapeutic compounds of this invention can be administered to a mammal alone or in combination with pharmaceutically acceptable carriers or as pharmaceutically acceptable salts, the proportion of which is determined by the solubility and chemical nature of the compound, chosen route of administration and standard pharmaceutical practice.

The compositions can also contain other therapeutically active compounds which are usually applied in the treatment of the diseases and disorders discussed herein. Treatments using the present compounds and other therapeutically active compounds can be simultaneous or in intervals.

It is also contemplated that ACT and ACT-related genes and gene products, as well as other products derived therefrom (e.g., probes, antibodies), will be useful in the diagnosis of Alzheimer's disease, presenile and senile dementias, psychiatric diseases such as schizophrenia, depression, etc., and neurologic diseases such as stroke and cerebral hemorrhage all of which are seen to a greater or lesser extent in subjects bearing mutations in the ACT gene. Diagnosis of inherited cases of these diseases can be accomplished by methods based upon the nucleic acids (including genomic and mRNA/cDNA sequences), proteins, and/or antibodies disclosed and enabled herein. Preferably, the methods and products are based upon the human ACT nucleic acids, proteins or antibodies disclosed herein. As will be obvious to one of ordinary skill in the art as to how exploit the present invention in the best possible mode. Thus, for brevity of exposition, but without limiting the scope of the invention, the following description will focus upon uses of the human homologues of ACT. It will be understood, however, that homologous sequences from other species, including those disclosed herein, will be equivalent for many purposes.

As will be appreciated by one of ordinary skill in the art, the choice of diagnostic methods of the present invention will be influenced by the nature of the available biological samples to be tested and the nature of the information required. ACT, for example, is highly expressed in brain tissue but brain biopsies are invasive and expensive procedures, particularly for routine screening. Other tissues which express ACT at significant levels, however, may demonstrate alternative splicing (e.g., (white blood cells do not express ACT) liver cells) and, therefore, ACT mRNA or protein from such cells may be less informative. Thus, assays based upon a subject's genomic DNA may be the preferred methods for diagnostics as no information will be lost due to alternative splicing and because essentially any nucleate cells may provide a usable sample. Diagnostics based upon other ACT-related proteins are subject to similar considerations: availability of tissues, levels of expression in various tissues, and alternative translation products resulting from alternative mRNA splicing.

When a diagnostic assay is to be based upon ACT-related proteins, a variety of approaches are possible. For example, diagnosis can be achieved by monitoring differences in the electrophoretic mobility of normal and mutant proteins. Such an approach will be particularly useful in identifying mutants in which charge substitutions are present, or in which insertions, deletions or substitutions have resulted in a significant change in the molecular mass of the resultant protein. Alternatively, diagnosis may be based upon differences in the proteolytic cleavage patterns of normal and mutant proteins, differences in molar ratios of the various amino acid residues, or by functional assays demonstrating altered function of the gene products. In some preferred embodiments, protein-based diagnostics will employ differences in the ability of antibodies to bind to normal and mutant ACT-related proteins. Such diagnostic tests can employ antibodies which bind to the normal proteins but not to mutant proteins, or vice versa. In particular, an assay in which a plurality of monoclonal antibodies, each capable of binding to a mutant epitope, can be employed. The levels of anti-mutant antibody binding in a sample obtained from a test subject (visualized by, for example, radiolabelling, ELISA or chemiluminescence) can be easily compared to the levels of binding to a control sample. Such antibody diagnostics can be used for in situ immunohistochemistry using samples of CNS tissues obtained antemortem or postmortem, including neuropathological structures associated with these diseases such as neurofibrillary tangles and amyloid plaques, or may be used with fluid samples such a cerebrospinal fluid or with peripheral tissues such as serum, plasma, or blood.

When the diagnostic assay is to be based upon nucleic acids from a sample, either mRNA or genomic DNA can be used. When mRNA is used from a sample, many of the same considerations apply with respect to source tissues and the possibility of alternative splicing. That is, there may be little or no expression of transcripts unless appropriate tissue sources are chosen or available, and alternative splicing may result in the loss of some information. With either mRNA or DNA, standard methods well known in the art may be used to detect the presence of a particular sequence either in situ or in vitro (see, e.g. Sambrook et al., eds. (1989) Molecular Cloning: A Laboratory Manual, Cold Spring Harbor Press, Cold Spring Harbor, N.Y.).

For in situ detection of ACT other ACT-related nucleic acid sequence, a sample of tissue will be prepared by standard techniques and then contacted with a probe, preferably one which is labeled to facilitate detection, and an assay for nucleic acid hybridization is conducted under optimal stringency conditions which permit hybridization only between the probe and highly or perfectly complementary sequences. As an example only, the following procedure can be employed on a subject: A mouse is anesthetized and transcardially perfused with cold PBS, followed by perfusion with a formaldehyde solution. The brain or other tissue of interest is then removed, frozen in liquid nitrogen, and cut into thin micron sections. The sections are placed on slides and incubated in proteinase K. Following rinsing in DEP, water and ethanol, the slides are placed in prehybridization buffer. A radioactive probe corresponding to the selected oligonucleotide corresponding to ACT sequence is incubated with the sectioned brain tissue. After incubation and air drying, the labeled areas are visualized by autoradiography or fluorescence. Positive spots on the tissue sample indicate hybridization of the probe with brain mRNA, demonstrating expression of the nucleic acid sequence.

A significant advantage of the use of either DNA or mRNA is the ability to amplify the amount of genetic material using the polymerase chain reaction (PCR), either alone (with genomic DNA) or in combination with reverse transcription (with mRNA to produce cDNA). PCR-based genetic methods may be preferred commercial embodiments for diagnostic screenings and the technical details as to how run PCR analysis are well know to those of ordinary skill in the art.

The above discussion provides a factual basis for the method of developing transgenic animals which have a modified phenotype. The methods used and the utility of the present invention are shown by the following non-limiting examples and accompanying figures.

EXAMPLES

General Methods

Immunohistochemistry: Standard methods known in the art and not specifically described are generally followed as in Stites et al. (eds), Basic and Clinical Immunology (8th Edition), Appleton & Lange, Norwalk, Conn. (1994) and Johnstone & Thorpe, Immunochemistry in Practice, Blackwell Scientific Publications, Oxford, 1982.

General Methods in Molecular Biology: Standard molecular biology techniques known in the art and not specifically described are generally followed as in Sambrook et al., Molecular Cloning: A Laboratory Manual, Cold Springs Harbor Laboratory, New York (1989, 1992), and in Ausubel et al., Current Protocols in Molecular Biology, John Wiley and Sons, Baltimore, Md. (1989).

Genotyping Litters: The resulting offspring are genotyped by cutting tail tips from weanlings, extracting DNA using a Promega genomic DNA extraction kit, transferring denatured DNA to nylon membrane and hybridizing duplicate samples with a DNA probe that recognizes either ACT or APP or other transgene.

Construction of Transgenic Mice

A cDNA fusion-construct with a 6 kbp mouse glial fibrillary acidic protein (GFAP) promoter and 100 bp of the 5'-end of the GFAP attached to the human ACT cDNA clone is constructed. The unique ApaI-SalI-fragment (−107 to +87) in the GFAP-SEAP expression vector (Sarid, 1991) is subcloned into Litmus-38 vector and the 2 existing ATG-start codons in the GFAP transcript are altered to ATC and AGG respectively with PCR-based site-directed mutagenesis. The original ApaI-SalI fragment is then replaced with the mutant fragment. A 1.5 kbp full-length human ACT-cDNA-clone is excised with EcoRI from the pGEM4-vector (Abraham et al., 1988) and blunt-ended. SalI-linkers are attached and the fragment is subcloned into the modified GFAP-expression vector construct. The non-coding 3'-UTR of the mRNA is derived from the rat preproinsulin II gene, which provides a 3' intronic region and a polyadenylation (polyA) site. The final construct is sequenced to confirm proper translation initiation on the start codon in the ACT-cDNA and linearized with EcoRV and ScaI. The 10 kbp fragment is separated on a low-melting point agarose gel, purified with β-agarase according to manufacturers instructions (FMC) and injected into pronuclei of FVB/N zygotes. Injected zygotes are transferred to pseudopregnant females. Heterozygous ACT-transgenic mice are identified with two PCR primer pairs located in different parts of the construct. Mice from one of these founder lines (#8784) are crossed with homozygous PDGF-hAPP(V717F) mice (Games et al.) and all offspring are screened with PCR for the GFAP-ACT-gene construct and the PDGF-hAPP construct. In addition, proper ACT protein expression in astrocytes is verified by ACT-immunohistochemistry in all of the pathologically examined heterozygous PDGF-hAPP(V717F)$^{+/-}$, ACT$^{+/-}$-mice.

Northern Blot

Total RNA is extracted with RNA Stat-60-kit (Tel-Test, Inc), and polyA$^+$-mRNA is selected with Dynabeads Oligo (dt)$_{25}$ (DYNAL, Inc). The RNA samples are heat-denatured (70° C.) in 50% formamide, 2.2M formaldehyde, 1M MOPS-buffer (pH 7.0) and separated by electrophoresis on a 1.0% agarose-formaldehyde gel, blotted onto Hybond-N$^+$ filters and baked for 2 hr at 80° C. Filters are prehybridized overnight and hybridized with P$^{32}$-labeled hACT and hGAPDH-cRNA-probes (Rogers J T, et al. 1999) in 50% formamide, 120 mM Tris-HCl, 8 mM EDTA, 600 mM NaCl, 1% nonfat dried milk powder and 1% SDS. The filters are subsequently washed to a stringency of 0.1×SSC, 0.1% SDS at 85° C. and exposed to autoradiographic Hyper-MP film (AMERSHAM).

Immunoprecipitation—Western Blot Analysis

Brain tissue from transgenic mouse is homogenized (2×10 strokes on ice) in 10 (v/w) STEN/Lysis buffer (1×STEN (pH 7.6), 1% NP-40, 0.2% BSA, 50 μg/ml PMSF, 5 μg/ml Leupeptin, 5 μg/ml Aprotinin and 2 μg/ml Pepstatin A). The homogenate is centrifuged at 50,000 g for 1 hr at 4° C. The supernatant is recovered, 2 μl polyclonal ACT-antibody (AXL-145, ACCURATE) is added and the mixture was allowed to incubate for 2 hrs at 4° C. 25 μl of equilibrated protein A-Sepharose slurry (PIERCE) is added and the mixture allowed to incubate overnight at 4° C. The antibody-antigen complex is retrieved by centrifugation 15,000 g for 10 min and subsequently washed 6 times (50 mM Tris-HCl, 150 mM NaCl, 6 mM EDTA (pH 7.4), 2.5% Triton X-100) and finally twice with 50 mM Tris-HCl and 6 mM EDTA (pH 7.4). The final pellet is resuspended in 20 μl 2×Laemli's buffer and boiled for 10 min, centrifuged 15,000 g for 1 min and the supernatant loaded onto a 8% polyacrylamide gel (Novex). The samples are transferred to an Immobilon-P filter (Millipore), blocked with 5% non-fat dry milk powder in 1×TTBS-buffer (1×TTBS is 0.1M Tris-HCl (pH 7.5), 0.9% NaCl, 0.1% Tween-20), incubated with primary monoclonal ACT-antibody (dil 1:2000, cat 178218, Calbiochem), or other antibody as noted herein, for 1 hr at RT in 1×TTBS-buffer, washed 3 times for 10 minutes with TTBS-buffer, blocked with 5% non-fat dry milk powder in 1×TTBS, incubated with secondary goat anti-mouse antibody (dil 1:5000, cat 31434, PIERCE) in blocking buffer solution for 30 min at RT, washed 4×10 min in 1×TTBS buffer, incubated with ECL-reagents (PIERCE) for 5 min, and finally exposed to ECL-Hyperfilm (AMERSHAM).

Histology and Immunohistochemistry

Mice are anesthetized with Nembutal (1 mg/10 g body weight) and intracardially perfused with 0.9% NaCl (50 ml) and then with 25 ml 4% paraformaldehydein 1 times. Sorenson's phosphate buffer. Dissected brains are allowed to immerse in same fixative solution overnight at 4° C., and are further cryoprotected by sequential overnight incubation in 10%, 20% and 30% (w/v) sucrose in 0.1×Sorenson's phosphate buffer. The brains are then frozen on a temperature-controlled freezing stage, coronally sectioned (25 μm) on a sliding microtome, and the sections are stored in 1×PBS with 10 mM NaN$_3$ until mounted on slides. The mounted sections are preincubated with 0.3% H$_2$O$_2$ in 50% DAKO-block (cat. X0909,DAKO) for 15 min to block endogenous peroxidase activity, permeabilized with 0.4% Triton X-100 in 1×PBS (pH 7.4) and incubated with DAKOblock (10 min) to reduce non-specific antibody staining. Primary antibodies used are rabbit anti-ACT (AXL-145, dil 1:1000, ACCURATE), mouse anti-β-amyloid (6E10, dil 1:5000, SENETEK), mouse anti-GFAP (G-A-5, dil 1:400, Sigma), or other antibody as noted herein. Tissue sections are stained with the VECTASTAIN ABCElite or MOM-kits (VECTOR). Secondary antibodies are anti-rabbit IgG (BA-1000, 1:300, VECTOR) or anti-mouse IgG as provided with the kits (Vector). Incubation with primary antibodies were for 1 hr at RT and with secondary antibodies for 30 min at RT. 50% DAKOblock solution is added to the ABC-reagent to lower the unspecific signal. The immunostaining is developed with DAB (0.4 mg/ml), 0.03% H$_2$O$_2$ in NiSO$_4$-Acetate-buffer (pH 6.0, 9 mg/ml with respect to Ni$^{2+}$) or with VectorDAB, VectorSG substrate kits. CongoRed-staining is accomplished by initially hydrating the section in H$_2$O for 30 min, incubating in saturated alcoholic sodium chloride solution (4% (w/v) NaCl in 80% EtOH) that is alkalinized with 10 mM NaOH (final conc.) prior to use. Sections are stained in a 0.2% Congo Red (SIGMA) solution that had been equilibrated with saturated alcoholic sodium chloride solution by stirring overnight, filtered (Whatman1 filter), and alkalinized with 10 mM NaOH (final conc.) prior to use. To induce gliosis, mice (3 month old mice) are inhalation-anesthetized with isoflurane and placed in a stereotactic instrument. Holes are drilled through the skull bone and a Hamilton syringe is inserted (Bregma coordinates posterior 2.7 mm; lateral ±2.5 mm; ventral 3 mm) and 1 μl of saline solution infused. The syringe is left in place for another minute and then slowly withdrawn. The animals are sacrificed 3 days later.

Image Analysis

Six equally spaced tissue sections (Bregma −1.06 to −2.30 mm, Franklin et al., 1996) from each animal are used for quantitative evaluations. The part of the cerebral cortex examined is defined as that laterally extending to a perpendicularly line drawn from the apex of the hippocampal pyramidal cell layer in the CA3-region of the hippocampus. Hippocampal measurement area is according to regular anatomical definitions. The sections are examined in a Nikon Microphot-FX-microscope at 200× magnification and video images captured with a color CCD-camera.

The images are segmented with respect to threshold settings for hue, saturation and luma that have been specified prior to analysis so as to distinguish specific signals from background. This predefined segmentation is subsequently used throughout the analysis without operator editing in order to determine the area of each plaque structure (ONCOR). The total measurement area is quantified at 20× magnification and the amyloid load expressed as Area fraction (=stained area$_{tot}$/measured area$_{tot}$). The Congo-positive plaques counted are defined as those objects displaying gold-green bifringence under crossed polarized light and having their perimeter located outside one radius from the centre of any other adjacent congo-positive plaque structure.

Statistical Analysis

The data samples collected are analyzed for deviation from a Gaussian distribution using a Kolgomorov-Smirnov test, and group comparison is evaluated with an unpaired t-test. The plaque size data (in $\mu m^2$) was logarithm transformed (with a logarithmic base of 10) and analyzed in relative frequency histograms with bins of 0.2. The distribution of the population of Congo-positive plaques, with respect to plaque size, is fitted to a Gaussian distribution equation with nonlinear regression analysis (GRAPHPAD PRISM, version 2.0).

Cognitive Testing of Transgenic and Control Animals

Animals. Mice in five groups are behaviorally evaluated: doubly transgenic APP+ACT mice; non-transgenic control B6-D2-F1 mice; transgenic APP mice; transgenic APP/ApoE knockout/ACT mice; and transgenic APP/ApoE knockout mice. Approximately equal number of males and females are included in each group. APP mice are derived from mutant either APP$_{K670N,M671L}$ transgenic line Tg2576, derived from C57B6/SJL×C57B6 background, or from mutant PDAPP (V1717F) transgenic line (Games et al. 1995, Alzheimer-type neuropathology in transgenic mice overexpressing V1717F beta-amyloid precursor protein. Nature 373:523–527) derived from a B2D6/F1×Swiss Webster background. After weaning, animals are genotyped and group housed until several weeks prior to behavioral testing, at which time they are individually housed. All animals have free access to water and rodent chow and are maintained on a 12-hour light/dark cycle. All behavioral testing is done in the light phase of this circadian cycle.

At either 5–7 months or 15–17 months of age, animals preferably begin a 6-week series of behavioral tests to evaluate their sensorimotor abilities, anxiety level, and cognitive performance. The following sequence of tests may be used: open field activity, balance beam task, string agility task, Y-maze, elevated plus-maze, standard water maze acquisition and retention, circular platform task, visible platform, and radial arm water maze.

The radial arm water maze is a preferred test, which is further described with respect to its operation and particular advantages in the following references which are hereby incorporated by reference in their respective entireties: Morgan D. et al. "Aβ peptide vaccination prevents memory loss in an animal model of Alzheimer's disease" Nature 408:982–985 (2000); Gordon, M. N. et al. "Correlation between cognitive defects and Aβ deposits in transgenic APP+PS1 mice" Neurobiol. Aging, 22:377–387 (2001); and, Arendash, G. W. et al. "Progressive, age-related behavioral impairments in transgenic mice carrying both mutant amyloid precursor protein and presenilin-1 transgenes" Brain Research, 891:42–53 (2001).

Specific Task Procedures. Abbreviated procedures are indicated below for previously described tasks. See, D. King, G. W. Arendash, F. Crawford, T. Sterk, J. Menendez, and M. J. Mullan, Progressive and gender-dependent cognitive impairment in the APPsw transgenic mouse model for Alzheimer's disease, Behav. Brain Res. 103 (1999) 145–162. A more detailed description of the remaining two tasks (elevated plus maze and radial arm water maze) is provided herein.

Open Field Activity. As a test of activity and exploratory behavior, each animal is placed in an open black box painted with lines (4 horizontal and 4 vertical) to demarcate 16 squares. The total number of line crossings over a single 5 minute trial was recorded.

Balance Beam Task. Each animal is placed at the center of a suspended beam and released. The average balance time from three successive trials is recorded. Maximum trial length is 60 seconds.

String Agility Task. As a test of agility and grip capacity, animals are permitted to grasp a suspended string only by their forepaws and then released. During a single 60 second trial, each animal is assessed using a 0–5 rating system (0=animal unable to remain on string; 1=hangs by 2 forepaws; 2=attempts to climb onto string; 3=2 forepaws and 1 or both hindpaws around string; 4=4 paws and tail around string, with lateral movement; 5=escape).

Y-maze. Each animal is placed in a walled Y-maze for a single 5 minute trial, during which the sequence and total number of arm choices are recorded. Spontaneous alternation, expressed as a percentage, is calculated. If an animal made the following sequence of arm selections (1,2,3,2,1,3,1,2), the total alternation opportunities would be 6 (total entries minus 2) and the percentage alternation would be 67% (4 out of 6). The data were also analyzed for position bias (left or right) according to the method of McFarland D. "Effects of scopolamine, d-amphetamine, and apomorphine on alternation and position biases", Pharmacol. Biochem. Behav. 32 (1989) 723–726.

Elevated Plus-maze. As a test to evaluate anxiety/emotionality, the elevated plus-maze consisted of four arms (30×5 cm) connected by a common 5×5 cm central area. All arms and the central area are constructed of plywood and painted black. Two opposite facing arms are open while the other two facing arms are enclosed by aluminum sheet walls (15 cm height). The entire plus-maze is elevated on a wooden pedestal to a height of 82 cm above floor level. During a single 5 minute trial, animals are placed onto the central area facing a closed arm. The number of closed arms entries, open arm entries, and amount of time spent in open arms is recorded. Between trials, any feces are removed from the maze and the maze floor is cleaned with a dilute vinegar solution to remove any urine or scent cues.

Water Maze (Submerged Platform). The floor of a 100 cm circular pool is divided into four quadrants, with a 9 cm platform submerged in the goal quadrant (quadrant 2; Q2). For each of 10 days of acquisition, 4 trials are performed wherein an animal is placed successively into each of the 4 quadrants to initiate a 60 second trial. Average latency to find the submerged platform is calculated from these 4 trials. On the day following acquisition testing, memory retention is evaluated in a single 60 second trial in which the submerged platform is removed and the animal released from the quadrant opposite the former platform quadrant. Percent of time spent in each quadrant, swim path, and swim speed are determined from videotapes of retention trials.

Circular Platform Task. A walled 69 cm circular platform, with 16 equidistantly spaced holes along its periphery, is encircled by a black curtain. Visual cues, located on the black curtain and platform walls, are used by the animal to find the one hole through which it can escape the platform surface to avoid the aversive stimuli of bright lights and fan wind. During a single 5 minute maximum daily trial, the total number of errors (head pokes into non-escape holes) and latency to find the escape hole are recorded. Although the escape hole remains constant for any given animal over the 8 days of testing, it is relocated after each animal's trial to control for olfactory cues. Also, to control for olfactory cues, the maze is cleaned with a dilute vinegar solution following each animal's trial.

Water Maze (Visible Platform). This is a cognitive-based task requiring the animal to locate a variably placed 9 cm visible platform in a 100 cm circular pool divided into four quadrants. The visible platform is elevated 0.8 cm above the water surface and had an attached 10.times.40 cm ensign. For each of the four test days, the animal is placed into the pool at the same location for each of four trials, with the platform moved to a new quadrant for each trial. Latency to find and ascend the visible platform is recorded (60 second maximum), with each day's four trials being averaged.

Radial Arm Water Maze. Because this is a novel "win-stay" Radial Arm Water Maze (RAWM) protocol for use with mice, a detailed methodology is provided herein. This RAWM protocol was conceived because, in the standard Morris maze, constancy of the escape platform location across testing days simplifies the task and thus minimizes the demands placed upon the hippocampal (working) memory system. To address this problem, the present RAWM protocol allows the platform to remain in the same location for each day's trials; however, the platform location is changed each day to test for spatial working memory. Moreover, the maze design necessitates mice to swim either in a central open area or in one of 6 arms. Each time a mouse makes an error (i.e., swims into an arm that does not contain the submerged platform), it is returned to the start arm until it swims directly from the start arm to the goal arm's hidden platform or until that trial's time has elapsed. Thus mice must repeatedly return, across trials within a day, to the arm that contains the submerged platform (i.e., a "win-stay" strategy"). This RAWM protocol requires mice to learn the rule that the platform is in the same arm on each trial during a day, but in a different arm each day. Following a given day's acquisitional trials, working memory for the platform location can be tested on the same day, at the end of a delay period (retention test).

To create an exemplary 6-arm water maze, 6 aluminum-walled triangles (30.5 cm side length×21 cm height) are placed equidistant from one another against the wall of a 100 cm circular pool. This arrangement forms 6 swim alleys (30.5 cm length×19 cm width) radiating from a common circular swim area (40 cm diameter), with swim alley walls extending approximately 5 cm above the water surface. An array of spatial cues are located on the testing room's walls and ceiling. RAWM testing consists of 4 acquisition trials and one memory retention trial each day for 9 days of testing. For any given day of testing, the submerged escape platform is positioned near the end of the designated goal arm for that day; the goal arm is randomly changed for each day of testing. A semi-random sequence from 4 of the remaining 5 arms is then selected as start points for each of that day's four acquisition trials (T1 through T4), with the number of errors during the last acquisition trial (T4) being an index of daily learning. For any given acquisition trial, the animal is placed into the designated start arm facing the common circular swim area. Over the ensuing one minute trial, the animal is allowed to swim into arms, with each non-goal arm selection (i.e., error) resulting in the mouse being returned (across the surface of the water) back to that trial's start arm to continue the trial. If a mouse enters the goal arm, but can not locate the submerged platform in that arm, an error is scored and the animal returned to that trial's start arm to continue the trial.

For each acquisition trial, the number of arm selection errors prior to escape onto the goal arm's submerged platform is recorded. Once they find the platform, animals are allowed to remain on the platform for 30 seconds. Alternatively, if the mice do not find the platform in the 60 second trial, they are guided to the submerged platform. Following completion of the four acquisition trials, animals are dried with heat lamps and returned to their home cage for a 30 minute delay period. A memory retention trial (T5) is then done, wherein the start arm was the same as trial 4. Over this one minute (maximum) trial, the number of arm errors to locate the submerged platform in the goal arm is recorded.

Statistical Analysis. The behavioral performance of transgenic mice and non-transgenic controls is preferably evaluated for the 5–7 month and 15–17 month behavioral time points separately. This allows for the first of two determinations of whether progressive behavioral impairment is shown by transgenic micenamely, that transgenic mice differ from controls at the later, but not the earlier, time point. For the string agility task, Mann-Whitney U-tests for non-parametric data are utilized. For standard water maze acquisition (submerged platform), circular platform, and visible platform tasks, repeated measure ANOVA's are performed. For the standard water maze memory retention trial ANOVA is used to analyze quadrant preference within each group and to compare percent of time spent in Q2 (the quadrant formerly containing the platform) across groups. For radial arm water maze (RAWM) testing, statistical analysis using ANOVA is performed for averaged errors in T1 (randomized initial trial), T4 (last learning trial), and T5 (working memory trial) over all three days following achievement of acquisitional criteria by non-transgenic (NT) controls. Unless otherwise indicated, all other behavioral comparisons are done by means of ANOVA and all group differences are deemed significant at $p<0.05$.

As a second determination of whether progressive behavioral changes have occurred in transgenic mice between the 5–7 month and 15–17 month time points, performance of transgenic mice tested at the earlier time point is compared directly to that of transgenic mice tested at the later time point. Similar comparisons are also performed between both age groups of non-transgenic animals to determine the presence of any normal age-related behavioral changes. All such comparisons involved MANOVA (for multiple time point tasks) or ANOVA (for single day tasks), with the exceptions of string agility, which involved non-parametric data analysis by Mann-Whitney U-tests.

RESULTS

Example 1

Alpha-1-antichymotrypsin Promotes β-sheet Amyloid Plaque Formation in a Transgenic Mouse Model of Alzheimer's Disease In this Example, the impact of ACT on β-amyloidosis is shown by generating transgenic GFAP-ACT mice and crossing them with the PDGF-hAPP(V717F) mouse. ACT expression is astrocyte-specific and inducible as previously shown in human brain. Congo-Red positive amyloid deposition is increased in the PDGF-hAPP(V717F)$^{+/-}$/ACT$^{+/-}$ mice as compared to PDGF-hAPP(V717F)$^{+/-}$/ACT$^{-/-}$ mice, particularly in the hippocampus, where ACT expression is most increased. It is shown herein that ACT exacerbates β-amyloidosis and constitutes a novel therapeutic target.

In this Example the generation of novel transgenic GFAP-ACT founder lines that mimic the astrocyte-specific, inducible, expression pattern of ACT in the human brain, are shown. One of these founder lines is crossed with the PDGF-hAPP(V717F) transgenic mouse strain to show the pathophysiological role of ACT in amyloid deposition in vivo. A novel astrocyte-specific GFAP (6 kbp) promoter construct extending 80 bp into a modified GFAP-coding region is designed to allow interactions between possible gene regulatory sequences within the GFAP coding region and upstream enhancer elements (Nakatani et al., 1990). The GFAP start codons are then altered so that the construct directs the translation to begin at the ACT start codon.

FIG. 1 shows expression of human ACT from the ACT constructs having either the GFAP-HACT promoter construct, or a CMV-ACT construct, introduced into IL-1 treated U373 MG human astrocytoma cells.

Figure 2A:
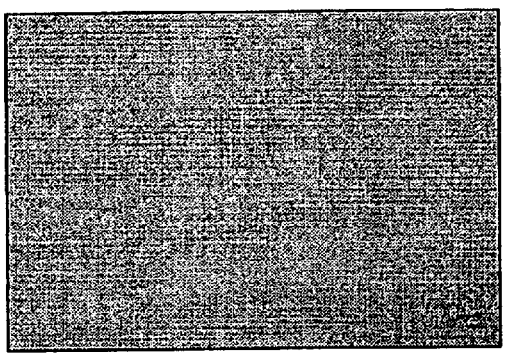
Figure 2B:
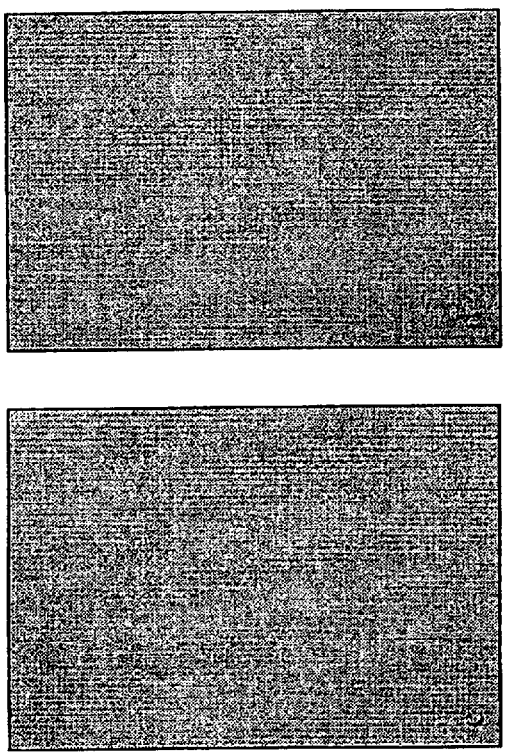
Figure 2C:
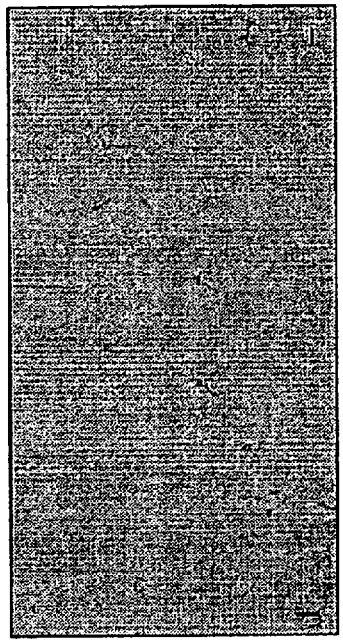
Figure 2D:
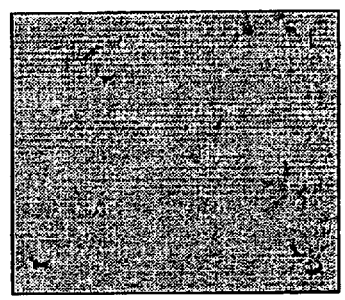
Figure 2E:
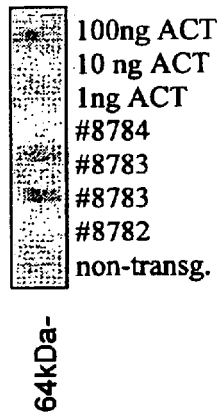
Figure 2F:
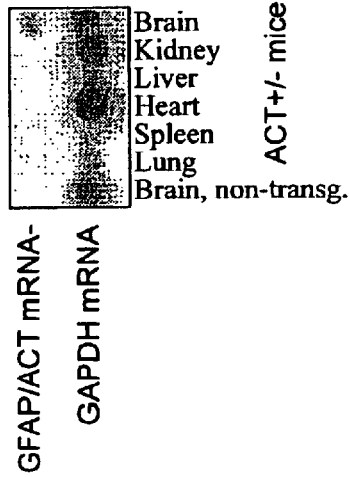

The ACT transgenic animals produced as described herein are viable with no overt pathological signs and express fully glycosylated ACT protein (~68 kDa) in the brain that comigrates with human plasma ACT protein (FIG. 2a). In addition, the animals display a restricted expression pattern of the chimeric GFAP-ACT mRNA transcript that was limited to brain tissue (FIG. 2b). Stab-wound injury is performed to demonstrate additional desirable expression characteristics such as astrocyte-specificity (shown by double immunostaining for GFAP and ACT; FIG. 3c) and inducible synthesis and secretion of the ACT-protein (FIG. 3d) in ACT$^{+/-}$ but not in ACT$^{-/-}$-mice (FIG. 3e). The validity of the double-staining protocol is established by finding no labelling using tissue sections from both ACT$^{+/-}$ and ACT$^{-/-}$ animals processed without one or both of the primary ACT and GFAP-antibodies.

Mice from the founder line #8784 are crossed with homozygous PDGF-hAPP(V717F) mice because this founder mouse most easily transfers the transgene to its offspring (~50%). As soon as 4 months of age, T-immunopositive astrocytes are apparent in the PDGF-hAPP(V717F)$^{+/-}$, ACT$^{+/-}$-mice in the absence of any treatment such as stab wound, and are mostly restricted to white matter areas such as the anterior commissure, the cingulum and the corpus callosum. At 6 months of age, when β-amyloid plaques are sparsely distributed in the hippocampus, ACT-immunostained astrocytes are clearly visible along the hippocampal fissure (FIG. 3c). By 10 months, when the β-amyloid deposition is more pronounced, the ACT-immunostained astrocytes was more widespread and located around congo-positive plaques in the PDGF-hAPP(V717F)$^{+/-}$, ACT$^{+/-}$-mice (FIG. 3a), but were absent in PDGF-hAPP(V717F)$^{+/-}$, ACT$^{+/-}$-mice of the same age (FIG. 3b). Furthermore, polyclonal ACT-antibody not only stained the surrounding astrocytes but also the congo-positive plaques themselves in the hippocampus of PDGF-hAPP$^{+/-}$, ACT$^{+/-}$ animals (FIGS. 3d–e).

Figure 5A:
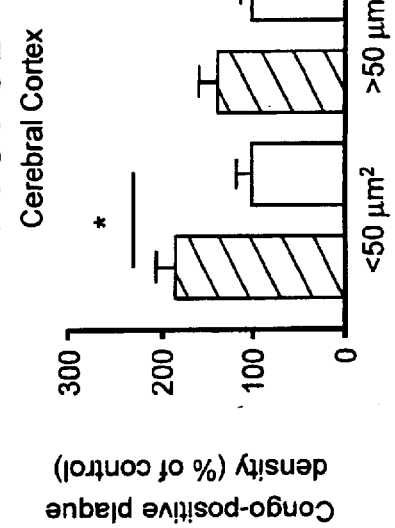
Figure 5B:
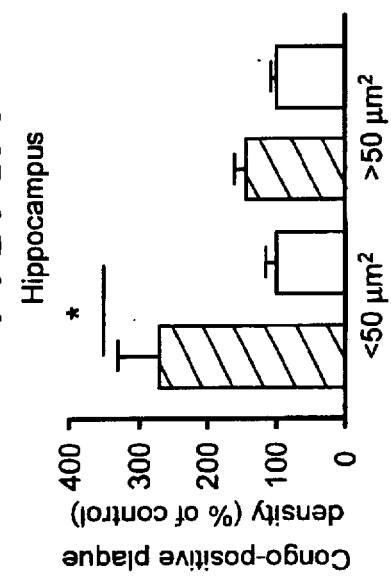
Figure 5C:
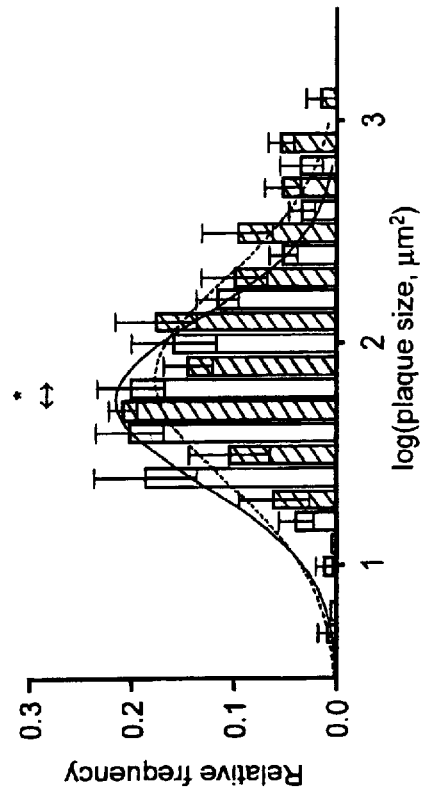
Figure 5D:
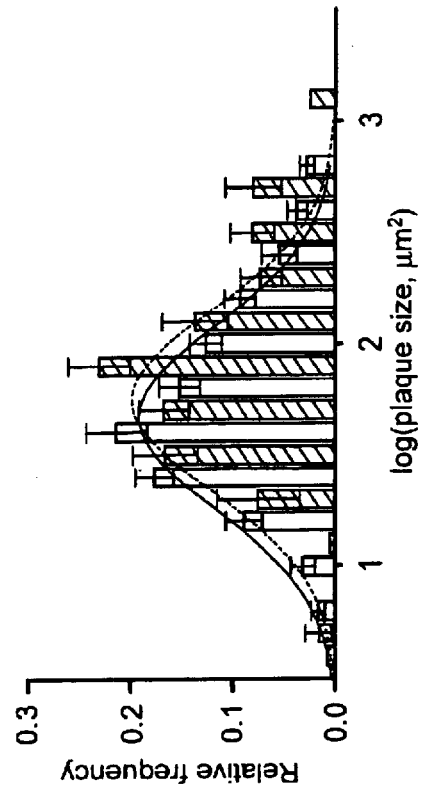

Fibrillar amyloid load, as measured by CongoRed staining, is quantified using high-power microscopy and image analysis in ~10 months old PDGF-hAPP(V717F)$^{+/-}$, ACT$^{+/-}$ (n=7) and PDGF-hAPP(V717F)$^{+/-}$, ACT$^{-/-}$ (n=6) animals. Amyloid load (Area Fraction) is significantly increased in the hippocampus (+55%, P<0.05) and modestly increased in the cerebral cortex (+14%, n.s.) of the PDGF-hAPP(V717F)$^{+/-}$, ACT$^{+/-}$ animals as compared to the PDGF-hAPP(V717F)$^{+/-}$, ACT$^{+/-}$ animals (FIG. 4a). The increased amyloid load is largely attributable to an increased numerical density of Congo-positive plaques both in the hippocampus (+85%, P<0.05) and the cerebral cortex (+58%, P<0.05, FIG. 4b). The plaque density data are then stratified according to plaque size (FIG. 5). The increased numerical density is more pronounced among small-sized plaques (<50 $\mu$m$^2$) both in the hippocampus (+170%, P<0.05, FIG. 5a) and the cerebral cortex (+85%, P<0.05, FIG. 5b), while the increased density of larger plaques (>50 $\mu$m$^2$) is less pronounced (+43% in the hippocampus, +39% in the cerebral cortex) and not statistically significant. The plaques size distribution is more completely analyzed using relative frequency histograms. The linear histograms were substantially skewed to the right and a logarithmic transformation of the plaque size data generated a very good fit of the sizes of the congo-positive plaques to a Gaussian distribution (FIGS. 5c–d). The correlation coefficient is equal to or greater than 0.94 for all analyses when using a Gaussian distribution equation for the nonlinear regression analysis. This approach has been shown to successfully describe the senile plaque size distribution in human AD brain (Hyman, B. T. et al. "Quantitative analysis of senile plaques in Alzheimer disease: observation of log-normal size distribution and molecular epidemiology of differences associated with apolipoprotein E genotype and trisomy 21 (Down syndrome)" Proc.Natl.Acad.Sci. 92, 3586–3590, 1995). The center of the Gaussian distribution curve for the PDGF-hAPP(V717F)$^{+/-}$, ACT$^{+/-}$ mice is shifted towards a smaller average plaque size in both the hippocampus (47±3 $\mu$m$^2$ vs. 56±5 $\mu$m$^2$, P<0.1, FIG. 5c) and the cerebral cortex (56±3 $\mu$m$^2$ vs. 70±7 $\mu$m$^2$, P<0.05, FIG. 4d) as compared to PDGF-hAPP(V717F)$^{+/-}$, ACT$^{-/-}$ mice.

In the present in vivo example, several of the previous findings with respect to ACT in normal and Alzheimer's disease-afflicted human brain are reproduced. Specifically, basal ACT-expression in human brain is very low (Abraham, C., Selkoe, D. & Potter, H. "Immunohistochemical identification of the serine protease inhibitor alpha$_1$-antichymotryp-sin in the brain amyloid deposits of Alzheimer's disease" Cell 52, 487–501, 1988), as is the expression in the transgenic mice at an early age prior to amyloidosis. ACT gradually becomes expressed and secreted from astrocytes primarily in the hippocampus but also in the cerebral cortex of the APP/ACT transgenic mice as the amyloid formation proceeds. Finally, ACT becomes a constituent of the Congo-positive amyloid plaque structure itself, similar to previous observations in AD brain tissue. There is an increased CongoRed-positive amyloid load in 10 months old PDGF-hAPP(V717F)$^{+/-}$, ACT$^{+/-}$-mice as compared to PDGF-hAPP(V717F)$^{+/-}$, ACT$^{-/-}$-mice, particularly in the hippocampal formation where ACT-expression in astrocytes is observed early on as the amyloidosis develops.

Genetic studies support the conclusion that expression of amyloid-associated proteins and the inflammation-inducing cytokine interleukin-1 (IL-1) are of importance in AD pathogenesis. A common polymorphism in the ACT-signal peptide has been shown to be a modifier of ApoE4-conferred AD susceptibility (Kamboh et al., 1995) and to increase AD amyloid angiopathy (Yamada et al., 1998). Although some studies have confirmed and extended this result (for example, Thome et al., 1995; Morgan et al., 1996,; Talbot et al., 1996, Esquerre et al., 1998; Nacimius et al., 1998) others have failed to reproduce the initial findings (Haines et al., 1996; Muller et al., 1996). As predicted for a signal peptide variant, the ACT-A polymorphism appears to increase the passage of the protein through the endoplasmic reticulum, as measured by production of glycosylated ACT-protein (Nilsson and Potter, unpublished observations), but the in vitro effect is weak unless investigated in a high-expression system such as CMV-promoter driven ACT-expression in COS-7 cells. The failure to unequivocally verify that the ACT/A signal polymorphism modifies AD frequency, possibly because the heterogeneous populations sometimes studied harbored other, mixed, genetic modifiers that masked the small effect of ACTA, does not exclude the possibility that other ACT polymorphisms with a more pronounced effect on ACT expression or interaction with beta-amyloid may be important risk factors for AD. A polymorphic site in the ApoE-promoter that measurably increases apoe-expression has also been found to be associated with AD (Bullido, et al. 1998) and deserves attention in the light of the profound effect of ApoE gene dosage on β-amyloidosis in AD transgenic mouse models (Bales et al., 1997). Finally, polymorpic allele variants in the IL-1 promoter that increase IL-1 production have been shown to confer as much as 10-fold increased risk for AD (Nicoll et al. 2000; Luigi et al., 2000).

ACT-immunostaining of the hippocampus of ACT founder lines 8783, 8784, and non-transgenic control mouse, is shown in FIGS. 6a–c, respectively, which provides an indication of basal expression. Founder strain 8783 (FIG. 6a) expresses ACT at a higher basal level than 8784 (FIG. 6b), possible due to its glial specific integration site in the mouse genome, and expression is almost exclusively gliotic. In FIG. 6a there a thin white line is visible that is absent in FIG. 6b, which corresponds to a cell layer that is exclusively neuronal. These results show that basal neuronal expression is close to zero in the 8783-founder line, but not in the 8784-founder line.

Figure 7:
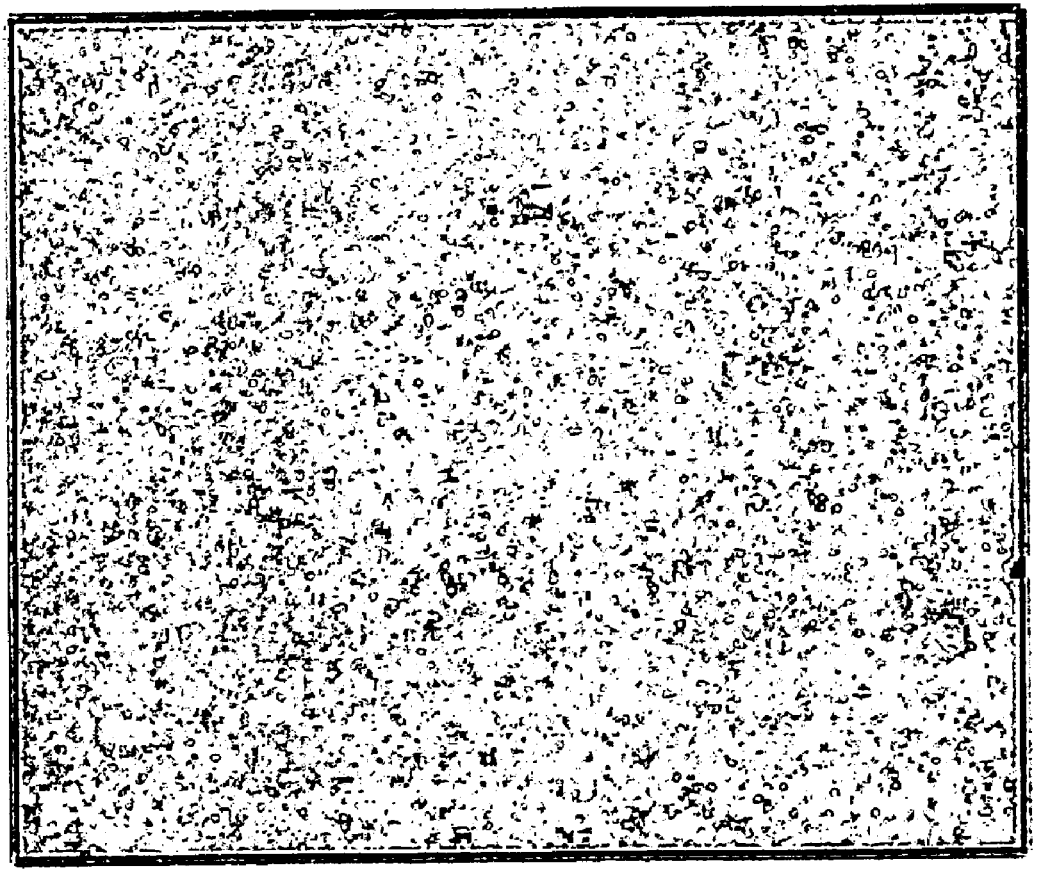
FIG. 7 Illustrates ACT-immunostaining in the CA1 region of the hippocampus of a founder line 8783 mouse.

FIG. 7 shows that founder line 8783 expresses ACT in the CA1 region of the hippocampus.

Figure 8:
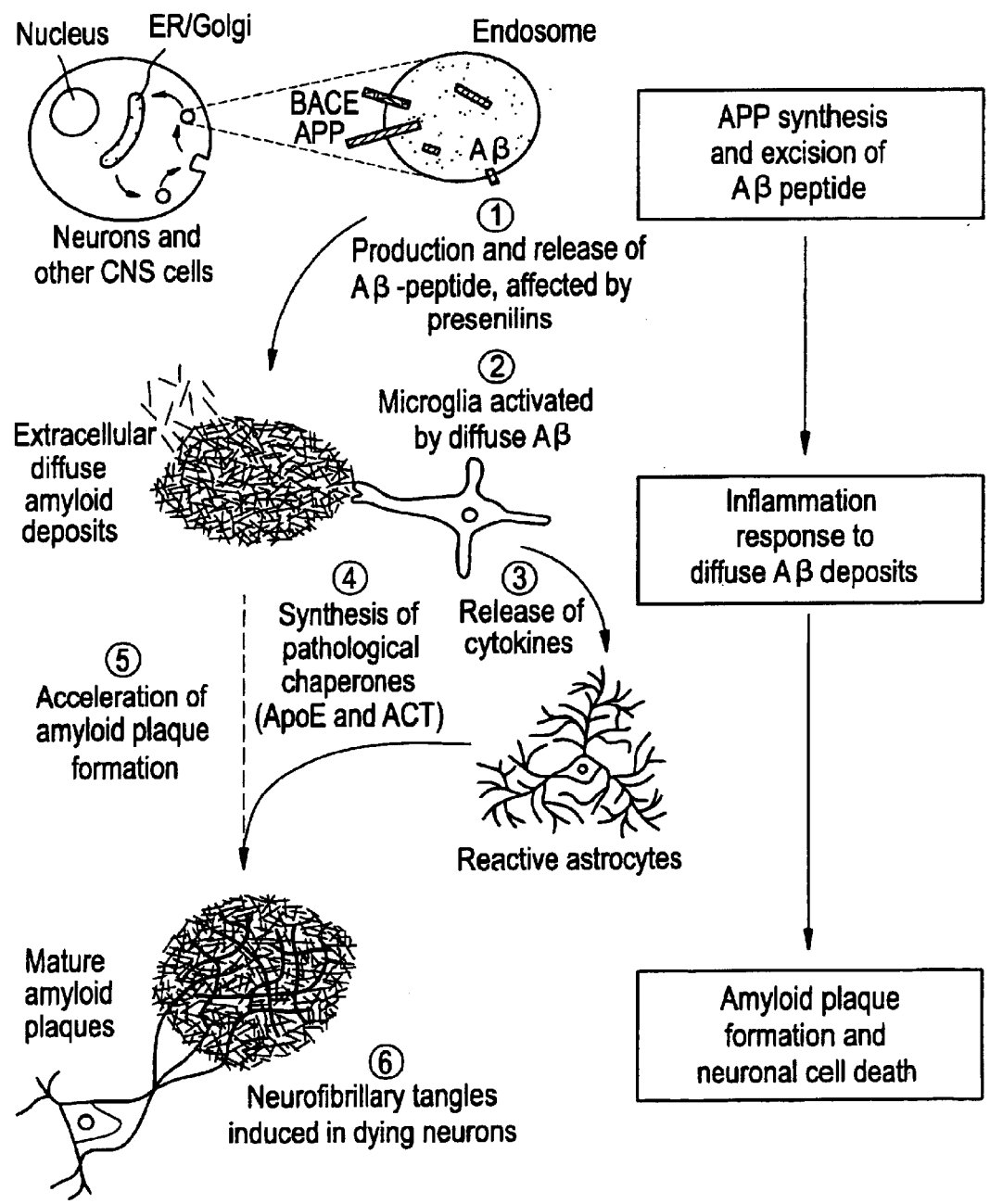
FIG. 8 Illustrates a model of the pathogenic pathway leading to Alzheimer's disease.

Not to be limited by theory, a possible mechanistic explanation for the findings herein and supporting the hypothesis that specific inflammatory processes accelerate the progression of AD as part of a "pathogenic pathway," is shown in FIG. 8. Each step in the pathway of FIG. 8—for example the microglial IL-1 overexpression and release, the induction of ACT-mRNA expression in astrocytes, and the molecular interactions between ACT (and apoE) and β-amyloid peptides/aggregates to promote amyloid formation—constitutes a specific therapeutic target to which new AD drug discovery may be directed.

Figure 9:
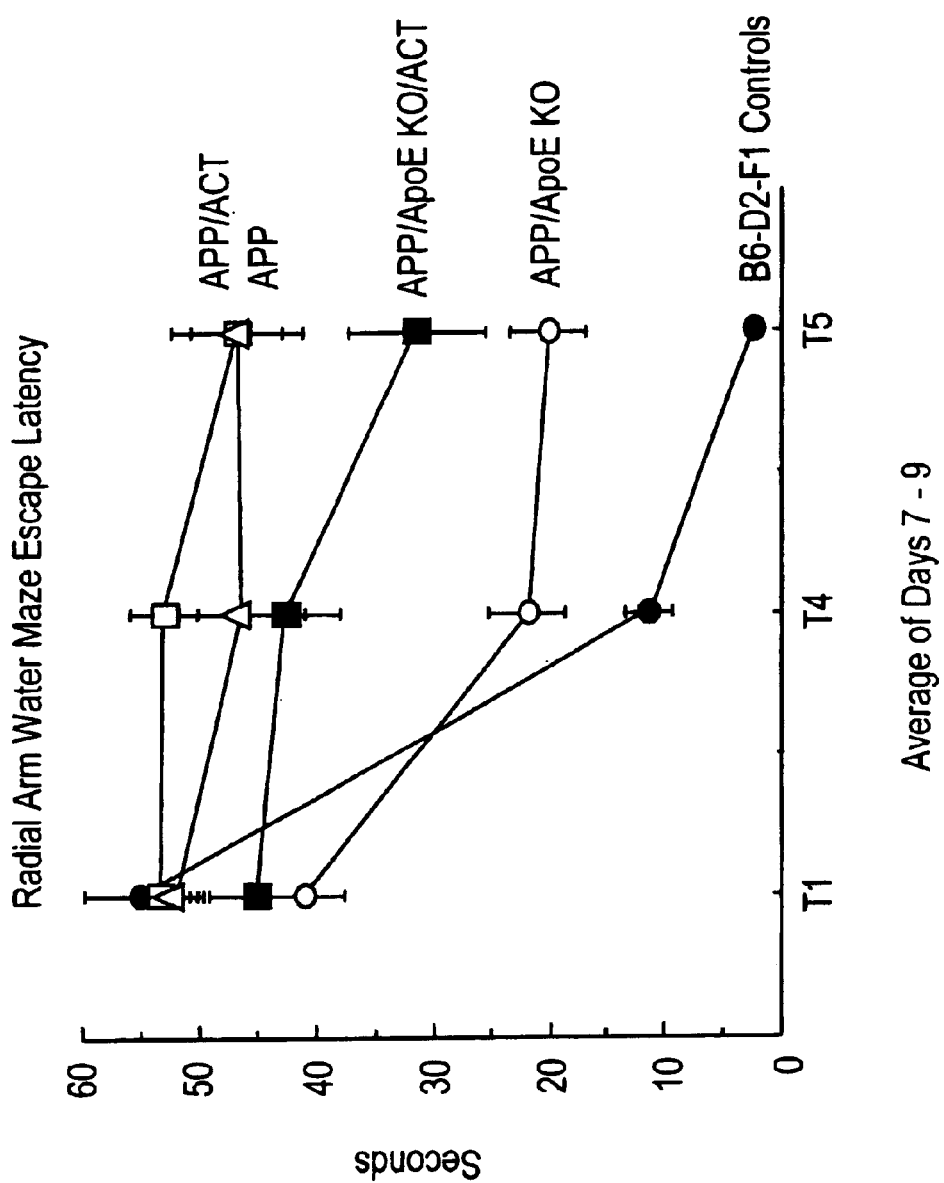
FIG. 9 Illustrates radial arm water maze escape latency test for cognitive impairment of various ACT transgenic mice.
Figure 10:
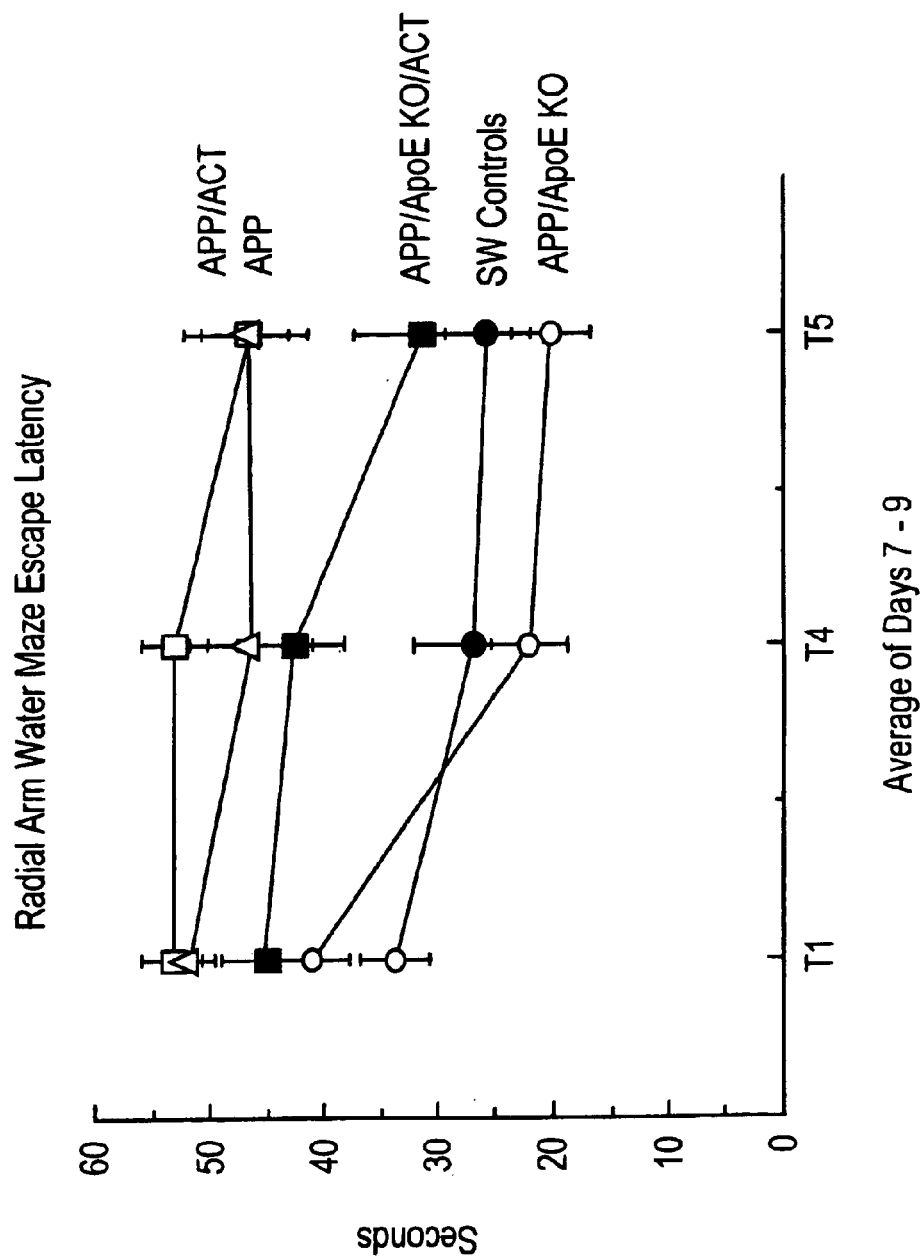
FIG. 10 Illustrates radial arm water maze escape latency test for cognitive impairment of various ACT and other transgenic mice.

Example 2
Alpha-1-antichymotrypsin Promotes Cognitive Impairment in a Transgenic Mouse Model of Alzheimer's Disease FIGS. 9 and 10 show cognitive impairment of transgenic ACT mice in a novel radial arm water maze test. The controls indicated on FIGS. 9 and 10 represent the strains of the transgenic parental mice and show that in neither case was impairment attributable to the mouse strain. The age of all animals in this example is between 15–17 months. T1, T2, and T5 stand for the first, second and fifth test within a particular day's testing. Specifically, APP/ACT and APP/ApoE knockout/ACT show increased cognitive impairment compared to APP and APP/ApoE knockout mice, respectively. Thus, consistent with the pathological findings of Examples 1 and 2, ACT expression potentiates cognitive impairment, further demonstrating the utility of the present invention as a model for Alzheimer's and other neurological disorders. Furthermore, the pathological chaperones ACT and ApoE are important not only for amyloid formation but also for cognitive decline.

Example 3
Antichymotrypsin Expression Induces Hyperphosporylated Tau, Paired Helical Filaments, Neurofibrillary Tangles and Neuronal Degeneration in a Transgenic Mouse Model of Alzheimer's Disease In this Example the involvement of ACT in promoting neurofibrillary pathology and neuronal degeneration. ACT overexpression in astrocytes leads within a few months of birth to the accumulation of abnormal filaments and neurofibrillary tangles containing hyperphosphorylated tau in neurons throughout the brains of the ACT transgenic mice. By a few months of age, clear neurodegeneration had developed. These results show why only human Alzheimer patients develop similar neurofibrillary pathology and neurodegeneration, in as much as normal mice do not carry a true ACT homologous gene. Furthermore, because ACT overexpression in AD is induced by the inflammatory cytokine IL-1 secreted by activated microglia, the present Example provides a new mechanism by which inflammation functions in the Alzheimer pathogenic pathway.

In the brain, chronic inflammation and ACT overexpression results in chronic hyperphosphorylation of tau and the consequent formation of PHF and NFT. Even before such clear pathological deposits are visible, the increased phosphorylation of tau evidently initiates pathways that can lead if unchecked, to neurodegeneration.

Figure 11:
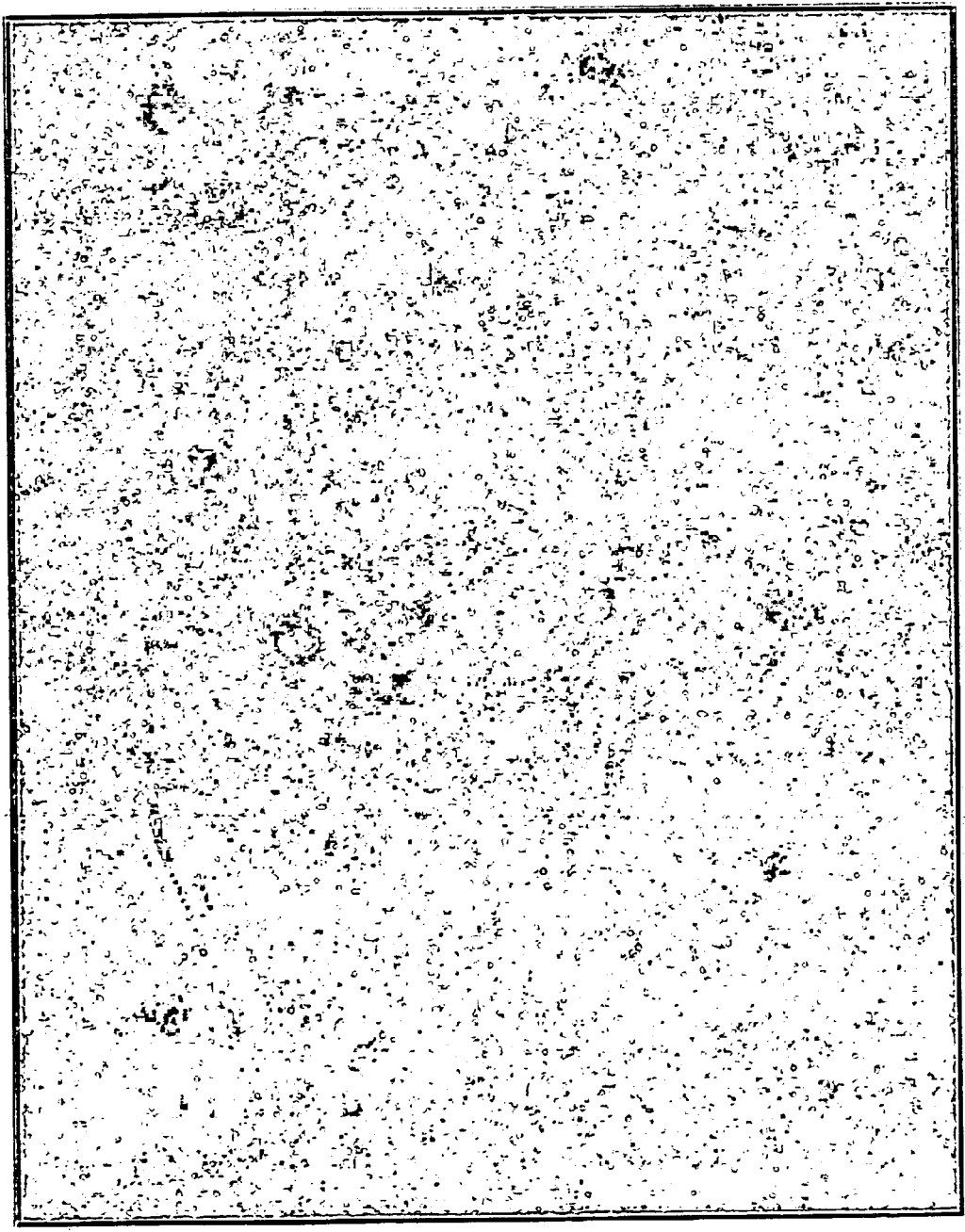
FIG. 11 Illustrates AT-8 immunohistochemical labeling for hyperphosphorylated tau in a specimen obtained from the cerebral cortex of founder line 8783.
Figure 12:
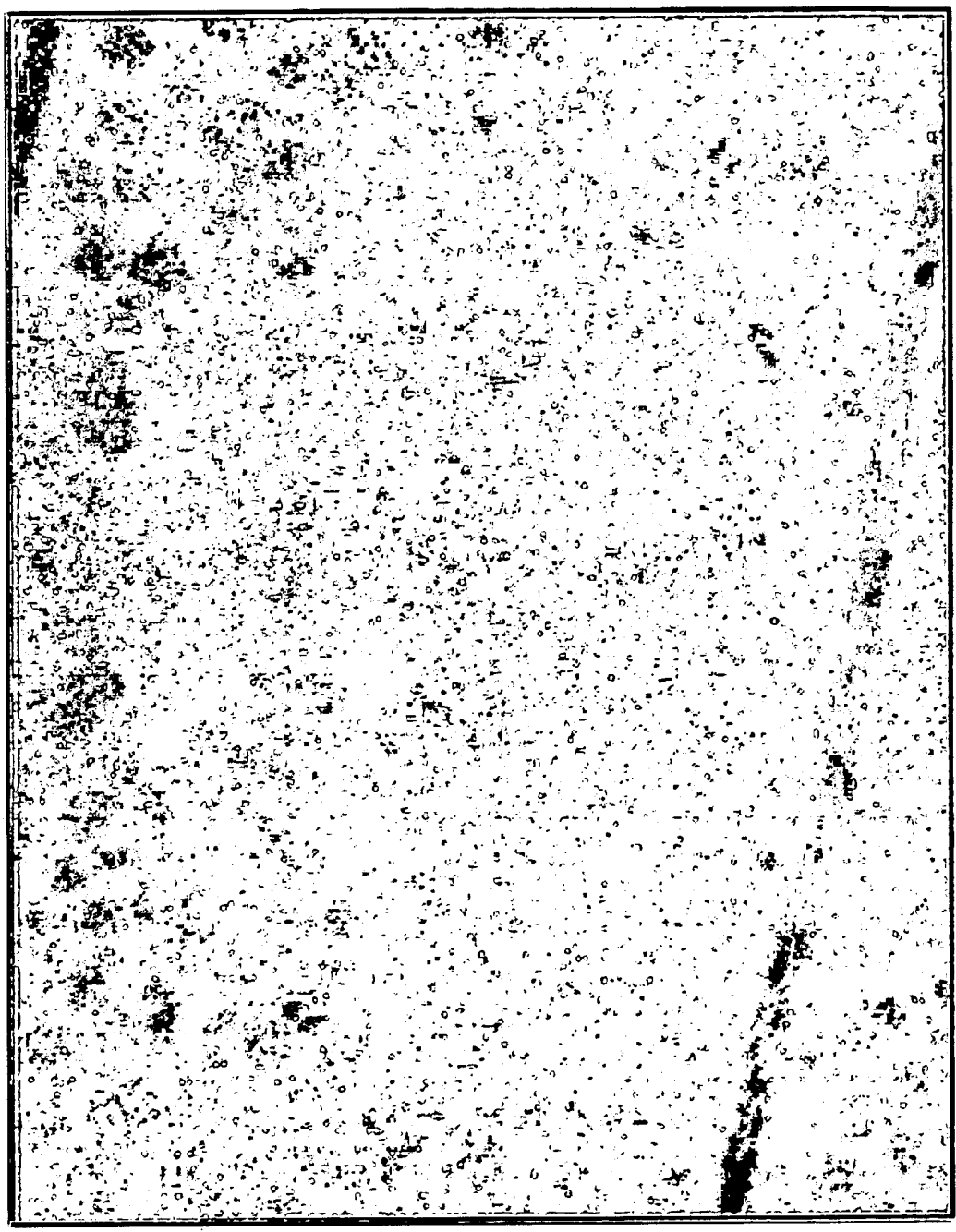
FIG. 12 Illustrates AT-8 immunohistochemical labeling staining for hyperphosphorylated tau in a specimen obtained from the CA-3 region of the hippocampus of founder line 8783.
Figure 13:
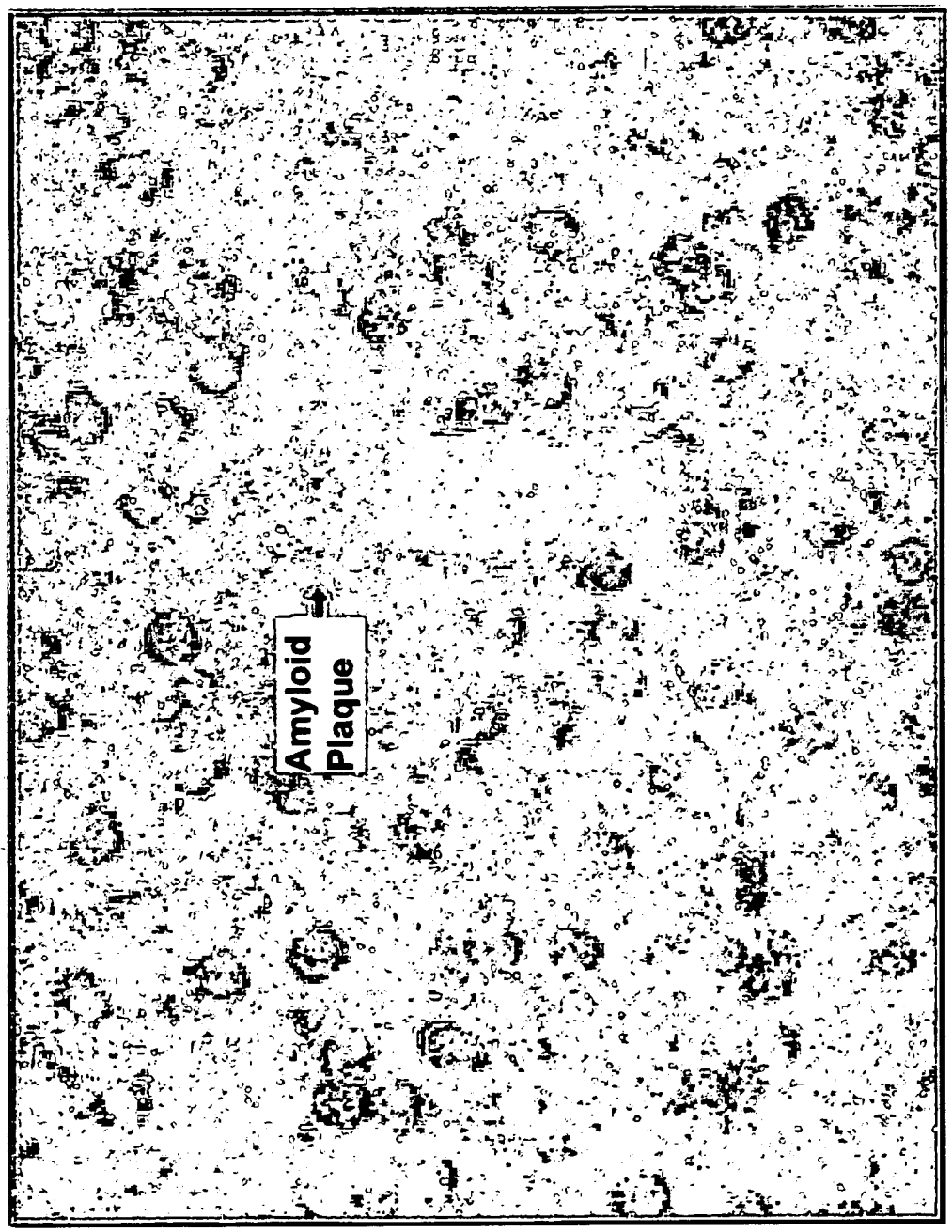
FIG. 13 Illustrates AT-8 immunohistochemical labeling staining for hyperphosphorylated tau in a specimen containing an amyloid plaque (arrowed).

That founder line 8783 expresses hyperphosphorylated tau is shown using AT-8 antibody. Thus, FIG. 11 shows AT-8 immunohistochemical labeling of a specimen obtained from the cerebral cortex, and FIG. 12 shows AT-8 immunohistochemical labeling of a specimen obtained from the CA-3 region of the hippocampus. Both show dendritic staining for hyperphosphorylated tau. As a positive control, FIG. 13 shows AT-8 labeling around an amyloid plaque (arrowed).

The presence of clear neuritic pathology for the first time in a mouse model of Alzheimer's disease provides the opportunity to develop and test novel therapeutic strategies to combat the disease. For example preventing IL-1 expression from microglia, recognition of IL-1 by astrocytes, or IL-1 intracellular signally activity would prevent the inflammation-associated overexpression of ACT in the developing AD brain. The result may be both lower amyloid formation and lower, or possibly no, neurofibrillary pathology or neurodegeneration. Similarly, reducing or eliminating the step(s) by which ACT induces tau hyperphosphorylation and polymerization in neurons should be beneficial in preventing AD from developing in at-risk individuals or even partially reversing cognitive decline in AD patients.

The disclosure of each patent, patent application and publication cited or described in this document is hereby incorporated herein by reference, in its entirety.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for testing a compound suspected of promoting or inhibiting phosphorylation of one or more proteins related to Alzheimer's disease, said method comprising: providing a mammalian cell; administering to said cell antichymotrypsin and said compound; and monitoring the phosphorylation state of said one or more proteins.

2. The method of claim 1, wherein said protein is tau, APP, cdc-2/cyclin B, cdk5, p53, cdc47, MAD, cyclin D, or cyclin E.

3. The method of claim 1, wherein said cell is neuronal.

4. A transgenic mouse whose genome comprises at least one transgene comprising a nucleic acid sequence encoding alpha-1-antichymotrypsin (ACT) operably linked to a glial fibrillary acidic protein (GFAP) promoter effective for expression of said nucleic acid sequence in the brain tissue of said transgenic mouse, wherein when said transgenic mouse is crossed with a second transgenic mouse whose genome comprises a nucleic acid sequence encoding an amyloid precursor protein (APP) V717 mutant or whose genome is homozygous for a non-functional apolipoprotein E (ApoE) gene, progeny are produced having an increased rate or extent of amyloid formation within the brain tissue.

5. The transgenic mouse of claim 4, wherein said GFAP promoter is devoid of ATG start codons.

6. The transgenic mouse of claim 5, wherein said nucleic acid sequence encoding ACT is expressed in astrocytes within the brain tissue of said transgenic mouse.

7. The transgenic mouse of claim 4, wherein the genome of the second transgenic mouse comprises a nucleic acid sequence encoding the amyloid precursor protein (APP) V717 mutant, and wherein the progeny have an increased rate or extent of amyloid formation within the brain tissue.

8. The transgenic mouse of claim 7, wherein the nucleic acid sequence encoding the APP V717 mutant is operably linked to a platelet-derived growth factor (PDGF) promoter.

9. The transgenic mouse of claim 4, wherein the genome of the second transgenic mouse is homozygous for a non-functional apolipoprotein E (ApoE) gene, and wherein the progeny have an increased rate or extent of amyloid formation within the brain tissue.

10. The transgenic mouse of claim 7, wherein said genome of said second transgenic mouse is homozygous for a non-functional apolipoprotein E (ApoE) gene, and wherein said progeny have an increased rate or extent of amyloid formation within the brain tissue.

11. A transgenic mouse whose genome comprises at least one transgene comprising a nucleic acid sequence encoding alpha-1-antichymotrypsin (ACT) operably linked to a glial fibrillary acid protein (GFAP) promoter effective for expression of said nucleic acid sequence in the brain tissue of said transgenic mouse, wherein said genome:

(a) further comprises a second transgene comprising a nucleic acid sequence encoding an amyloid precursor protein (APP) V717 mutant; or (b) is homozygous for a non-functional apolipoprotein E (ApoE) gene; or (c) further comprises a second transgene comprising a nucleic acid sequence encoding an amyloid precursor protein (APP) V717 mutant, and is homozygous for a non-functional apolipoprotein E gene;

and wherein said transgenic mouse has an increased rate or extent of amyloid formation within the brain tissue.

* * * * *

UNITED STATES PATENT AND TRADEMARK OFFICE
CERTIFICATE OF CORRECTION

PATENT NO. : 6,781,029 B2
DATED : August 24, 2004
INVENTOR(S) : Lars Nilsson, Huntington Potter and Gary W. Arendash It is certified that error appears in the above-identified patent and that said Letters Patent is hereby corrected as shown below:

Title page,
Item [57], ABSTRACT,
Line 5, "transgeny" should read -- transgenic --.

Column 3,
Line 41, "Morgan et al.;" should read -- Morgan et al., --.

Column 4,
Line 10, "Bales, K. R.;" should read -- Bales, K. R., --.
Line 13, "apoliprotein E" should read -- apolipoprotein E --.

Column 5,
Line 36, "5'0 UTR" should read -- 5' UTR --.

Column 7,
Lines 8-9, "-ACT$^{+/-}$ -mice" should read -- , ACT$^{+/-}$ -mice --.
Line 13, "ACT$^{+/-}$ -m-ice" should read -- ACT$^{+/-}$ -mice --.

Column 9,
Line 38, "optionally be grouped" should read -- optionally being grouped --.

Column 11,
Line 48, "APP+/+ apoE-/-" should read -- APP$^{+/+}$ apoE$^{-/-}$ --.

Column 14,
Line 66, "as to how exploit" should read -- as to how to exploit --.

Column 15,
Lines 54-55, "samples such a cerebrospinal" should read -- samples such as cerebrospinal --.

Column 16,
Lines 31-32, "as to how run PCR analysis are well know" should read -- as to how to run PCR analysis are well known --.

Column 17,
Line 2, "subdloned" should read -- subcloned --.
Line 17, "agarase" should read -- agarose --

UNITED STATES PATENT AND TRADEMARK OFFICE
CERTIFICATE OF CORRECTION

PATENT NO. : 6,781,029 B2
DATED : August 24, 2004
INVENTOR(S) : Lars Nilsson, Huntington Potter and Gary W. Arendash It is certified that error appears in the above-identified patent and that said Letters Patent is hereby corrected as shown below:

Column 18,
Lines 12-13, "paraformaldehydein 1 times. Sorenson's" should read
-- paraformaldehydein 1x Sorenson's --.

Column 19,
Line 34, "(V171F)" should read -- (V717F) --.
Line 36, "V1717F" should read -- V717F --.

Column 21,
Line 16, "10.times.40cm" should read -- 10 x 40 cm --.

Column 22,
Line 25, "micenamely," should read -- mice-namely, --.
Line 67, "-/ACT$^{+/-}$ mice" should read -- /ACT$^{+/-}$ -mice --

Column 23,
Line 1, "/ACT$^{-/-}$ mice" should read -- /ACT$^{-/-}$ -mice --.

Column 24,
Line 29, "ACT$^{+/-}$ mice" should read -- ACT$^{+/-}$ -mice --.
Line 33, "ACT$^{-/-}$ mice" should read -- ACT$^{-/-}$ -mice --.
Lines 41-42, "alpha$_1$-antichymotryp-sin" should read -- alpha$_1$-antichymotrypsin --.

UNITED STATES PATENT AND TRADEMARK OFFICE
CERTIFICATE OF CORRECTION

PATENT NO.    : 6,781,029 B2
DATED         : August 24, 2004
INVENTOR(S)   : Lars Nilsson, Huntington Potter and Gary W. Arendash It is certified that error appears in the above-identified patent and that said Letters Patent is hereby corrected as shown below:

<u>Column 25,</u>
Line 27, "possible" should read -- possibly --.
Line 29, "6a there a thin" should read -- 6a a thin --.

Signed and Sealed this

Twenty-ninth Day of March, 2005

JON W. DUDAS
*Director of the United States Patent and Trademark Office*